(12) United States Patent
Borochov-Neori et al.

(10) Patent No.: US 8,445,040 B2
(45) Date of Patent: May 21, 2013

(54) **EXTRACTS OF *SCLEROCARYA BIRREA***

(75) Inventors: Hamutal Borochov-Neori, Eilat (IL); Amnon Grinberg, Kibbutz Yotvata (IL)

(73) Assignee: Management and Holdings—Ardom, D.N. Eilot (IL)

( * ) Notice: Subject to any disclaimer, the term of this patent is extended or adjusted under 35 U.S.C. 154(b) by 0 days.

(21) Appl. No.: 12/867,756

(22) PCT Filed: Feb. 19, 2009

(86) PCT No.: PCT/IL2009/000192
§ 371 (c)(1),
(2), (4) Date: Aug. 16, 2010

(87) PCT Pub. No.: WO2009/104184
PCT Pub. Date: Aug. 27, 2009

(65) Prior Publication Data
US 2010/0311828 A1 Dec. 9, 2010

Related U.S. Application Data

(60) Provisional application No. 61/064,125, filed on Feb. 19, 2008.

(51) Int. Cl.
*A61K 36/00* (2006.01)

(52) U.S. Cl.
USPC .......................................... 424/777; 424/725

(58) Field of Classification Search
None
See application file for complete search history.

(56) References Cited

FOREIGN PATENT DOCUMENTS

| WO | 00/47062 A2 | 8/2000 |
| WO | 03/092634 A2 | 11/2003 |
| WO | 2006/097806 A1 | 9/2006 |

OTHER PUBLICATIONS

Mdluli (Journal of Food Biochem. (2003), vol. 27, pp. 67-82).*
Fundira (J. Agric. Food Chem. (2002), vol. 50, pp. 1535-1542).*
Mason (Vascular Health and Risk Management (2011), vol. 7, pp. 405-416).*
Ndhlala (Food Chemistry (2007), vol. 103, pp. 82-87—available online Oct. 2006).*
Gorinstein (Journal of the Science of Food and Agriculture (2002), vol. 82, pp. 1166-1170).*
Emborg (Journal of Neuroscience Methods (2004), vol, 139, pp. 121-143).*
Mdluli, Kwanele, M., et al., "Enzymatic Browning in Marula Fruit 1: Effect of Endogenous Antioxidants on Marula Fruit Polyphenol Oxidase," Journal of Food Biochemistry, (2003), pp. 67-82, vol. 27.
Pretorius, Victor, et al., "Volatile Flavour Components of Marula Juice," Z Lebensm Unters Forsch, (1985) pp. 458-461, vol. 181.
Borochov-Neori, Hamutal, et al., "Phenolic Antioxidants and Antiatherogenic Effects of Marula (*Sclerocarrya birrea* Subsp. caffra) Fruit Juice in Healthy Humans," Journal of Agricultural and Food Chemistry, (2008), pp. 9884-9891, vol. 56.
Dimo, Théophile, et al., "Effect of *Sclerocarya birrea* (Anacardiaceae) stem bark methylene chloride/methanol extract on streptozotocin-diabetic rats," Journal of Ethnopharmacology, (2007), pp. 434-438, vol. 110.
Ojewole, John, A. O., "Evaluation of the Analgesic, Anti-inflammatory and Anti-diabetic Properties of *Sclerocarya birrea* (A. Rich.) Hochst. Stem-Bark Aqueous Extract in Mice and Rats," Phytotherapy Research, (2004) pp. 601-608, vol. 18.
International Search Report, International Publication No. WO 2009/104184 A3, International Application No. PCT/IL2009/000192, mailed on Oct. 28, 2009, 6 pages.
Eloff, J.N., "Antibacterial activity of Marula (*Sclerocarya birrea* (A. rich.) Hochst. subsp. caffra (Sond.) Kokwaro) (Anacardiaceae) bark and leaves," Journal of Ethnopharmacology, (2001), pp. 305-308, vol. 76.
Ndhlala, A.R., et al., "Antioxidant potentials and degrees of polymerization of six wild fruits," Scientific Research and Essay, (Dec. 2006), pp. 087-092, vol. 1, No. 3.

* cited by examiner

*Primary Examiner* — Susan Hoffman
(74) *Attorney, Agent, or Firm* — Vorys, Sater, Seymour and Pease LLP; Susanne M. Hopkins; Ari G. Zytcer

(57) ABSTRACT

Provided are extracts obtained from the marula fruit (*Sclerocarya Birrea*) and uses thereof in a great variety of applications, e.g., use in food supplements for engendering an anti-atherogenic effect in healthy and non-healthy subjects (humans and non-human animals) and as agents for treating or preventing various diseases and disorders.

3 Claims, 15 Drawing Sheets

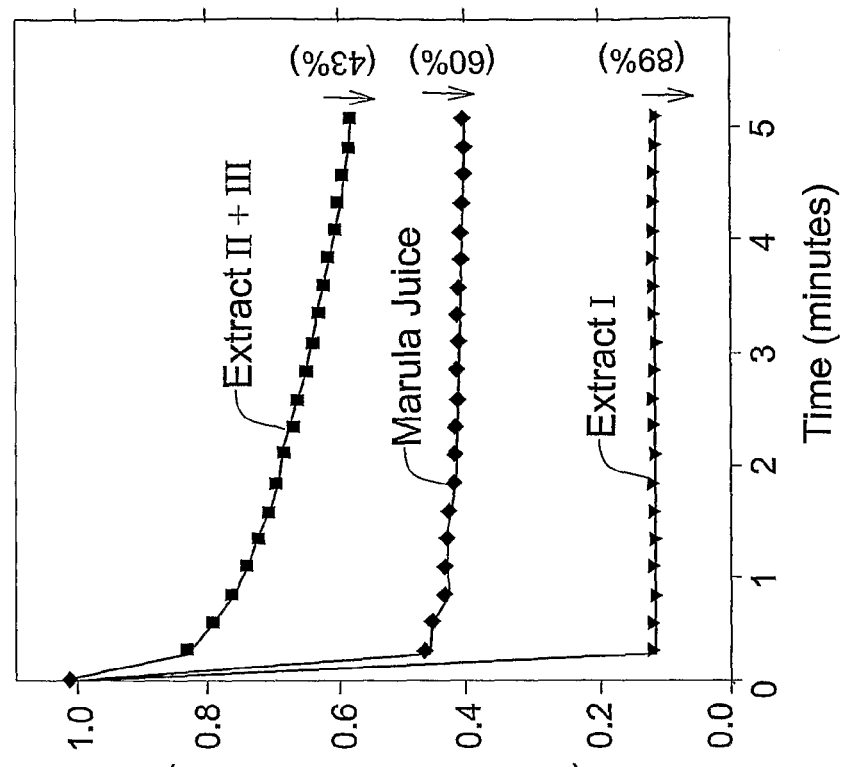
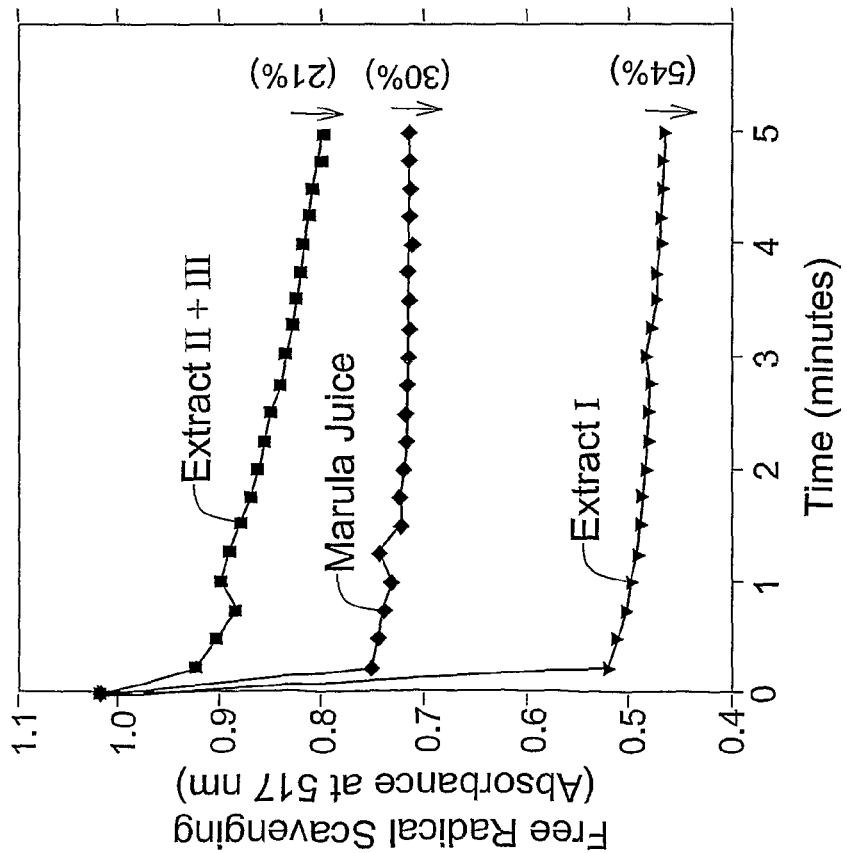
FIG. 3B
FIG. 3A

EXTRACTS OF *SCLEROCARYA BIRREA*

This is a National Phase Application filed under 35 U.S.C. §371 as a national stage of PCT/IL2009/000192, filed on February 19, 2009, claiming the benefit under 35 U.S.C. §119(e) of U.S. Provisional Application No. 61/064,125, filed on February 19, 2008, the content of each of which is hereby incorporated by reference in its entirety.

FILED OF THE INVENTION

The present invention generally relates to water-soluble extracts obtained from the *Sclerocarya birrea* fruit and uses thereof.

BACKGROUND OF THE INVENTION

The marula (*Sclerocarya birrea*, Family: Anacardiaceae) is a medium-to-large-sized deciduous tree with an erect trunk and rounded crown. The plant is used as a food source today as was used in ancient times. The fruit of the marula is edible, typically eaten raw or processed into a variety of food products such as a jelly and also brewed into an alcoholic beer, known by the Vhavenda people as Mukumbi.

Medicinal uses and applications of the marula include the use of bark and leaves for treating bacteria-related diseases and diabetes [1,2] and also diarrhea as disclosed in Australian patent publication no. 2000/29790 [3].

International publication no. WO 03/092634 [4] discloses the use of marula oil in topical preparations for inhibiting the formation of scar tissue on the skin.

The Marula fruit was shown to posses an increased total antioxidant capacity [5], to have the capacity to inhibit phospholipid peroxidation and to have superoxide anion radical scavenging activity [6]. International publication no. WO 06/097806 [7] discloses that various parts of the marula plant such as bark, leaves, fruit, roots and seeds contain hydrophobic antioxidants, which may be obtained from the plant by means of maceration and/or extraction.

Publications

[1] Ojewole J. A et al., *Phytother Res.* 2004, 18(8):601-8.
[2] Eloff J. N et al., *J Ethnopharmacol.* 2001, 76(3):305-8.
[3] Australian patent publication no. 2000/29790.
[4] International publication no. WO 03/092634.
[5] Mdluli, K. M and Owusu-Apenten, R., *Journal of Food Biochemistry.* 2003, 27: 67-82.
[6] Ndhlala E. R et al., *Scientific Research and Essay.* 2006, 1(30):087-092.
[7] International publication no. WO 06/097806.

SUMMARY OF THE INVENTION

Although the marula fruit has been reported to be rich in antioxidants, the preparation and use of extracts of the marula fruit in the treatment of diseases and disorders such as atherosclerosis and neurodegenerative diseases has not been reported thus far.

The surprising results, disclosed herein, indicate that the extracts prepared from marula juice are not only stable for long periods of time but more importantly posses therapeutic benefits different and in some cases better than those exhibited by the untreated marula juice. The extracts of the invention have demonstrated to favorably affect blood lipids, as shown by a reduction in serum LDL, by an increment in serum HDL, and by an attenuation of serum oxidative stress; the extracts have demonstrated efficacy in the treatment of oxidative stress damage, atherosclerosis, neurodegeneration and disorders associated therewith.

The marula juice extracts of the present invention are also effective to prevent neurodegeneration, as evidenced by their protective influence on neuronal cells exposed to free radical damage.

The present invention also discloses the use of marula juice extracts as antioxidants for use in a great variety of applications, e.g., use in food supplements for engendering, e.g., an anti-atherogenic effect in healthy and non-healthy subjects (humans and non-human animals) and as agents for treating or preventing neurodegenerative associated diseases.

Thus, in one aspect of the present invention, there is provided an extract derived from the marula fruit, excluding the seed, said extract being obtained by a process comprising subjecting juice collected from the marula fruit to an extraction with one or more of an aqueous solution, an organic solvent and a mixture thereof, i.e., to thereby obtain from the marula juice an extract having the desired biological benefits.

The marula juice obtained from the marula fruit may be filtered prior to extraction in order to remove fruit debris such as seed remnants and other insoluble matter. The filtration may be carried out using any method known in the art for filtering beverages, such as, but not limited to, diatomaceous earth (DE) filtration and membrane filtration.

In some embodiments, the marula juice obtained from the marula fruit is pasteurized prior to extraction in order to slow microbial growth is the juice by reducing the number of viable pathogens therein. Typically, pasteurization was carried out by exposing the juice to temperatures below boiling. In some embodiments, pasteurization is achieved by one or more other methods of pasteurization known in the art, e.g., controlled by national food safety agencies (such as the USDA in the United States and the Food Standards Agency in the United Kingdom). Some non-limiting examples include High Temperature/Short Time (HTST) pasteurization, Extended Shelf Life (ESL) pasteurization, Ultra-high temperature (UHT or ultra-heat treated) pasteurization, and batch or vat pasteurization.

The term 'extract' as used herein refers to a water-soluble product obtained from any part of the marula fruit or any part derived therefrom, excluding the seed, but including one or more of mesocarp, endocarp, rind (thick outer skin), and/or skin (exocarp), by employing a method selected from expression, absorption, maceration, lyophilization, distillation and any combination of two or more of these processes.

The extracted substances, separately or in combination, may be formed into any desired formulation including an aqueous solution, a solid such as a dry powder, a granule or a pellet, a concentrate, e.g., a semi-liquid having a syrupy consistency which may be obtained by evaporating all or nearly all the liquid content of the extract, or any other form. Generally, the methods of material extraction may vary *mutatis mutandis* depending on the age of the marula fruit, the subtype, the season of harvest, the region of growth, the substances to be extracted, their stability and other factors which are known to a person skilled in the art.

In some embodiments, the extract of the invention is obtained by contacting the marula juice with an aqueous solution to extract therefrom one or more ingredient or a combination thereof. The 'aqueous solution' may be in most general terms water (in some embodiments water of varying natural mineral concentrations) or distilled or otherwise purified (distilled or purified in any other method) water, an aquoues salt solution comprising one or more salts or a mixture of water with one or more water-miscible polar solvent, e.g., $C_1$-$C_4$ alcohols and ketones.

In some embodiments, the aqueous solvent is a mixture of water and at least one alcohol. In some further embodiments, the aquoes solvent is a mixture of water and ethanol, wherein the water:ethanol ratio is one of 1:1, 1:2 . . . 1:5 . . . 1:10 . . . 1:100 . . . 1:1,000 . . . etc., respectively, or 2:1, 3:1 . . . 5:1 . . . 10:1 . . . 100:1 . . . 1,000:1, etc., respectively. Any other intermediate ratio is also included.

The extraction may alternatively employ an organic solvent alone or in combination with another such solvent. In some embodiments, the extraction process is a multistep process whereby the marula fruit (juice) is contacted first with one solvent and then with a different solvent so as to maximize the yield or enrich the extract with one or more desired components.

Typically, the organic solvent is at least one alcohol such as methanol, ethanol and isopropyl alcohol, or a ketone such as acetone. When ethanol is used, it may be used as an aqueous ethanolic solution, e.g., of between about 40 to 60% ethanol. Similar solutions may also be used with the other water-miscible organic solvents. The extract obtained from following an alcoholic extract is herein designated extract I.

It should be understood in the context of the present invention that the ethanolic extraction, or any other extraction disclosed herein, may be carried out at any convenient temperature. It will be apparent to those skilled in the art that more efficient extraction will occur if the juice is agitated, such as by stirring or shaking, and/or if the mixture is heated to a temperature above room temperature (above 25-27° C.). Lower extraction temperatures, such as those below room temperature, may also be used. In some embodiments, the exteraction process is carried out at room temperature or at a temperature between 25 and 30° C.

It should also be understood in the context of the present invention that the extraction can be carried out for any convenient length of time.

A person skilled in the art would further recognize that the process for obtaining the extract of the invention may involve macerating the marula fruit to obtain smaller bits of the whole fruit from which extracts may be obtained by one or more of other extraction methods, such as distillation. Alternatively, the extract may be obtained by expression, namely by pressing out of the juice from the fruit.

Thus, in some embodiments, prior to contacting the juice with one or more solvent as disclosed, the fruit, i.e., whole fruit, excluding the seed, or any part thereof, may be pretreated by maceration, expression or any other process.

The juice obtained from the marula fruit may be stored prior to extraction or pretreatment, e.g., drying, for prolonged periods of time. The storage may be at any temperature and condition, under which the freshness of the juice is maintained and degradation is prevented or minimized. Such temperatures may be above or below room temperature. In some embodiments, the juice may be stored in a refrigerator for several weeks or in the freezer for several years. Where freezing of the juice is employed, the process may further comprise the step of defrosting the juice prior to extraction or processing.

Drying of the juice may be achieved by heating the liquid juice under vacuum, or under atmospheric pressure, at a preset temperature which may be room temperature or above ambient, in one batch or in smaller quantities so as to control the moisture content of the extract. In a non-limiting example disclosed herein, the drying is achieved by pouring the juice over a surface such as a tray, in some cases covered with a foil (e.g., an aluminum foil) to evenly heat the juice and obtain a substantially uniform layer of dried marula extract.

The wet concentrate (syrup) obtained by drying is yellowish to dark brown in color, depending on the concentration and type of extract. The dried material is readily pulverized and has a bright gold to dark brown color depending on the type of extract. The dried matter is water soluble.

The marula extract which is thereafter obtained contains varying amounts of volatile material, with the amounts depending on the length of the drying period and the temperature employed. Without wishing to be bound by theory, upon removal of the volatile components, the concentrate, namely in some embodiments, the powdered extract, contains in comparison to the whole fruit juice a higher concentration of active components which presence and combination provides the high activity which is not observed in the whole fruit and which is demonstrated herein.

Thus, the extract is obtained by a process comprising contacting marula juice with an aqueous solvent as defined to obtain a suspension from which a liquid extract may be separated.

In some embodiments, the process comprising:
(i) collecting juice from the marula fruit;
(ii) contacting said juice with one or more of an aqueous solution, a water-miscible polar organic solvent and a mixture thereof to obtain a suspension; and
(iii) separating from said suspension a liquid extract.

In some embodiments, the collected juice is dried or pretreated as disclosed prior to extraction.

In further embodiments, the separation of the liquid extract of step (iii) may be by way of centrifuging the suspension obtained in step (ii) to separate a the liquid extract as a supernatant from a solid mass.

In some further embodiments, the process comprises:
(i) collecting juice from the marula fruit;
(ii) drying the juice into a solid or a semi-solid;
(ii) contacting the dried or semi-dried juice obtained in step (ii) with one or more of an aqueous solution, an organic solvent and a mixture thereof to obtain a suspension; and
(iii) optionally centrifuging the suspension to separate a liquid extract from a solid mass.

In further embodiments, the process comprising:
(i) providing juice from the marula fruit, said juice being in a form selected from whole fresh juice, whole stored-juice, pasteurized juice, dried juice, and semi-dried juice;
(ii) contacting the juice with one or more of an aqueous solution, an organic solvent and a mixture thereof to obtain a suspension; and
(iii) optionally centrifuging the suspension to separate a liquid extract from a solid mass.

In some other embodiments, the process comprising:
(i) providing juice from the marula fruit, said juice being in a form selected from whole fresh juice, whole stored-juice, pasteurized juice, dried juice, and semi-dried juice;
(ii) contacting the juice with one or more of an aqueous solution, an organic solvent and a mixture thereof to obtain a suspension; and
(iii) separate a liquid extract from a solid mass.

It should be noted that the separation of the liquid extract may be repeated more than once, with a second amount of the same or different solvent, and the supernatants obtained from each step may be combined and further treated to isolate, concentrate or further process the extract. Thus, two or more, supernatants may be combined and the solvent and/or some of the water may be removed, for example by using any one method of solvent removal.

When the starting fruit material includes a solid matter or in cases where the marula fruit has been processed into a dried or semi-dried powder or granuled form, the extract may be separated at least into a solid phase and an aqueous phase, each phase having the biological acitivity as disclosed herein.

The extract of the invention, obtained by employing one or more processes as disclosed herein, may be characterized by one or more of the following:

1. high stability at room temperature for long periods of time;
2. may be formed into various forms including a liquid, a solid or a semi-solid form;
3. may be formed into a solution with a great variety of additives;
4. may be formed as a nutritional supplement for consumption by humans;
5. has a broad range of biological activities in comparison to the original juice, as further disclosed herein; and
6. has a FRAP (Ferric-Reducing Antioxidant Power) antioxidative capacity greater than that of the original juice.

Thus, the invention also provides a marula extract characterized by a FRAP antioxidative capacity of a minimum of 1,000 and 1,500 mg vitamin C equivalents per 100 ml. This compares to the FRAP measured for the untreated marula juice of between 260 and 600 mg vitamin C per 100 ml. in other words, the FRAP capacity of an extract according to the invention is between 2- and 3-fold the activity observed in the original untreated juice.

In some embodiments, the extract having the above FRAP capacity is extract I.

The present invention also provides an extract having a depleted-polyphenolic fraction, said extract being designated herein as extract II. The polyphenolic fraction, herein as extract III, may be seperated from the marula juice by, e.g., chromatography of the marula juice to affort extract II (depleted) and extract III (seperated phenolic fraction). In some embodiments, depletion of the polyphenolic fraction is achieved by a process comprising filtering the marula juice, for example by passing the juice through one or more layers of cheesecloth (of different grades, e.g., from open to extra-fine weave used according to the quality and quantity of the juice), optionally centrifuging the filtered juice to remove fruit debree, applying the clear juice to chromatography, e.g., column chromatography using columns packed with Sepabeads ion exchange and adsorbent resins, or $C_{18}$-bonded silica or resins for hydrophobic interaction and reversed phase chromatography, collecting the fractions and combining fractions having the same total soluble solids (TSS).

In some embodiments, the polyphenol fraction may be collected from the medium employed for chromatography, e.g., from the column beads, by mixing the medium, e.g., beads, with an alcoholic solution (ethanol, methanol, etc). The alcoholic fractions may be than combined and evaporated to dryness.

According to some embodiments, in order to obtain an extract with an increased polyphenolics:vitamin C ratio, the polyphenolic fraction (i.e., extract III) may be separated from the juice and then added to the polyphenol-depleted fraction (i.e., extract II). In some other embodiments, extract II is combined with extract I.

In some embodiments, extract II is characterized by a FRAP antioxidative capacity of at least between 250 and 500 mg vitamin C equivalents per 100 ml.

As used herein 'polyphenols' refers to a group of substances, characterized by the presence of more than one phenol unit or building block per molecule. Polyphenols are generally divided into hydrolyzable tannins (gallic acid esters of glucose and other sugars) and phenylpropanoids, such as lignins, flavonoids, and condensed tannins. In some embodiments, the polyphenols obtained from the macula juice comprise hydrolysable tannins, catechins and hydroxycinnamic acids and/or derivatives thereof.

In another one of its aspects, the present invention provides use of at least one extract of the invention for the preparation of a composition.

In some embodiments, the composition is a pharmaceutical composition.

In further embodiments, the extract is the active ingredient present in the composition along with a pharmaceutically acceptable carrier, diluent or excipient.

The choice of a carrier will be determined in part by the particular extract, as well as by the particular method used to administer the composition comprising it. Accordingly, there is a wide variety of suitable formulations of the pharmaceutical composition of the present invention. The following formulations for oral, aerosol, parenteral, subcutaneous, intravenous, intramuscular, intraperatoneal, rectal, and vaginal administration are merely exemplary and are in no way limiting.

Formulations suitable for oral administration can consist of (a) liquid solutions, such as an effective amount of the extract dissolved in diluents, such as water, saline, or orange juice; (b) capsules, sachets, tablets, lozenges, and troches, each containing a predetermined amount of the extract, as solids or granules; (c) powders; (d) suspensions in an appropriate liquid; and (e) suitable emulsions. Liquid formulations may include diluents, such as water and alcohols, for example, ethanol, benzyl alcohol, and the polyethylene alcohols, either with or without the addition of a pharmaceutically acceptable surfactant, suspending agent, or emulsifying agent. Capsule forms can be of the ordinary hard- or soft-shelled gelatin type containing, for example, surfactants, lubricants, and inert fillers, such as lactose, sucrose, calcium phosphate, and corn starch. Tablet forms can include one or more of lactose, sucrose, mannitol, corn starch, potato starch, alginic acid, microcrystalline cellulose, acacia, gelatin, guar gum, colloidal silicon dioxide, croscarmellose sodium, talc, magnesium stearate, calcium stearate, zinc stearate, stearic acid, and other excipients, colorants, diluents, buffering agents, disintegrating agents, moistening agents, preservatives, flavoring agents, and pharmacologically compatible carriers. Lozenge forms can comprise the active ingredient in a flavor, usually sucrose and acacia or tragacanth, as well as pastilles comprising the active ingredient in an inert base, such as gelatin and glycerin, or sucrose and acacia, emulsions, gels, and the like containing, in addition to the extract, such carriers as are known in the art.

The extracts or compositions of the present invention, e.g., pharmaceutical composition, alone or in combination with other suitable components can be made into aerosol formulations to be administered via inhalation. These aerosol formulations can be placed into pressurized acceptable propellants, such as dichlorodifluoromethane, propane, nitrogen, and the like. They may also be formulated as pharmaceuticals for non-pressured preparations, such as in a nebulizer or an atomizer.

Formulations suitable for parenteral administration include aqueous and non-aqueous, isotonic sterile injection solutions, which can contain anti-oxidants, buffers, bacteriostats, and solutes that render the formulation isotonic with the blood of the intended recipient, and aqueous and non-aqueous sterile suspensions that include suspending agents, solubilizers, thickening agents, stabilizers, and preservatives. The compound can be administered in a physiologically acceptable diluent in a pharmaceutical carrier, such as a sterile liquid or mixture of liquids, including water, saline, aqueous dextrose and related sugar solutions, an alcohol, such as ethanol, isopropanol, or hexadecyl alcohol, glycols, such as propylene glycol or polyethylene glycol, glycerol ketals, such as 2,2-dimethyl-1,3-dioxolane-4-methanol, ethers, such as poly(ethyleneglycol) 400, an oil, a fatty acid, a fatty acid ester or glyceride, or an acetylated fatty acid glyceride with or without the addition of a pharmaceutically acceptable surfactant, such as a soap or a detergent, suspending agent, such as pectin, carbomers, methylcellulose, hydroxypropylmethylcellulose, or carboxymethylcellulose, or emulsifying agents and other pharmaceutical adjuvants.

Oils, which can be used in parenteral formulations, include petroleum, animal, vegetable, or synthetic oils. Specific examples of oils include peanut, soybean, sesame, cottonseed, corn, olive, petrolatum, and mineral. Suitable fatty acids for use in parenteral formulations include oleic acid, stearic acid, and isostearic acid. Ethyl oleate and isopropyl myristate are examples of suitable fatty acid esters. Suitable soaps for use in parenteral formulations include fatty alkali metal, ammonium, and triethanolamine salts, and suitable detergents include (a) cationic detergents such as, for example, dimethyl dialkyl ammonium halides, and alkyl pyridinium halides, (b) anionic detergents such as, for example, alkyl, aryl, and olefin sulfonates, alkyl, olefin, ether, and monoglyceride sulfates, and sulfosuccinates, (c) nonionic detergents such as, for example, fatty amine oxides, fatty acid alkanolamides, and polyoxy-ethylenepolypropylene copolymers, (d) amphoteric detergents such as, for example, alkyl-β-aminopriopionates, and 2-alkyl-imidazoline quaternary ammonium salts, and (3) mixtures thereof.

The parenteral formulations typically contain from about 0.5 to about 25% by weight of the extract in solution. Suitable preservatives and buffers can be used in such formulations. In order to minimize or eliminate irritation at the site of injection, such compositions may contain one or more nonionic surfactants having a hydrophile-lipophile balance (HLB) of from about 12 to about 17. The quantity of surfactant in such formulations ranges from about 5 to about 15% by weight. Suitable surfactants include polyethylene sorbitan fatty acid esters, such as sorbitan monooleate and the high molecular weight adducts of ethylene oxide with a hydrophobic base, formed by the condensation of propylene oxide with propylene glycol. The parenteral formulations can be presented in unit-dose or multi-dose sealed containers, such as ampules and vials, and can be stored in a freeze-dried (lyophilized) condition requiring only the addition of the sterile liquid carrier, for example, water, for injections, immediately prior to use. Extemporaneous injection solutions and suspensions can be prepared from sterile powders, granules, and tablets of the kind previously described.

The extracts and compositions of the present invention may be made into injectable formulations. The requirements for effective pharmaceutical carriers for injectable compositions are well known to those of ordinary skill in the art. See *Pharmaceutics and Pharmacy Practice*, J. B. Lippincott Co., Philadelphia, Pa., Banker and Chalmers, eds., pages 238-250 (1982), and *ASHP Handbook on Injectable Drugs*, Toissel, 4$^{th}$ ed., pages 622-630 (1986).

Additionally, the extracts of the present invention may be made into suppositories by mixing with a variety of bases, such as emulsifying bases or water-soluble bases. Formulations suitable for vaginal administration may be presented as pessaries, tampons, creams, gels, pastes, foams, or spray formulas containing, in addition to the active ingredient, such carriers as are known in the art to be appropriate.

As stated above, the extracts and compositions of the invention may be manufactured, presented and/or stored in any form, namely in the form of a liquid, a concentrate, a dry powder, a solution, an emulsion, or a stock solution or a stock concentrate.

In some embodiments, the pharmaceutical composition is for the treatment or prevention of at least one disease or disorder associated with oxidative stress damage.

Oxidative stress is the result of an imbalance in pro-oxidant/antioxidant homeostasis that leads to the generation of toxic reactive oxygen species. Free radicals are formed when oxygen interacts with certain molecules and starts a chain reaction of damage among important cellular components. Thus, inflammation and the oxidative processes are interconnected. In addition, oxidative stress can induce cytotoxicity of blood cells, stimulate release of inflammatory cytokines, and induce the production of growth factors. Oxidative stress plays a critical role in the formation of plaques and along with inherent vascular inflammation may be a strong predictor of atherosclerosis.

Thus, as used herein, 'oxidative stress damage' refers to damage to cells, tissues and/or organs of an animal, including humans, that is caused by an imbalance between the production of reactive oxygen and the ability of a biological system to readily detoxify the reactive intermediates or easily repair the resulting damage. Most often, disturbances in this normal redox state may cause toxic effects through the production of peroxides and free radicals that damage all or certain components of the cell, including proteins, lipids, and DNA.

In some embodiments, the oxidative stress damage is associated with a disorder or a disease selected from atherosclerosis, parkinson's disease, heart failure, myocardial infarction, neurodegenerative diseases or disorders, ocular disease, chronic fatigue syndrome and others.

Atherosclerosis, the leading cause of morbidity and mortality among people with a western life style, develops as a result of various risk factors. Hypercholesterolemia is a major risk factor for atherosclerosis and reduction in plasma cholesterol concentration by drug therapy reduces cardiovascular incidence. The atherosclerotic lesion is characterized by accelerated oxidative stress and formation of a reactive oxygen species (ROS), which attacks lipids in lipoproteins, as well as in arterial macrophages. Oxidative modification of low-density lipoprotein (LDL) plays a key role in the pathogenesis of atherosclerosis. Oxidized LDL (Ox-LDL) is a major contributor to the development of atherosclerotic lesions, since it stimulates macrophage cholesterol accumulation and foam cell formation. In contrast to the atherogenicity of LDL, serum high-density lipoprotein (HDL) levels are inversely related to the risk of atherosclerosis. HDL exerts an inhibitory effect on LDL oxidation and this effect may be related to its associated enzyme paraoxonase 1 (PON1).

Atherosclerosis is also the process or disorder involving the build-up of plaque on the insides of arteries, including those in the heart, brain, arms, legs, and pelvis. Thus, the term may also refer to progressive accumulation of smooth muscle cells, immune cells (e.g., lymphocytes, macrophages, or monocytes), lipid products (e.g., lipoproteins, or cholesterol), cellular waste products, calcium, or other substances within the inner lining of an artery, resulting in the narrowing or obstruction of the blood vessel and the development of atherosclerosis-associated diseases.

As atherosclerosis is manifested within large and medium-sized arteries, treatment or prevention often affects the development of a state of chronic inflammation within the arteries.

The extract of the invention is therefore suitable also for the treatment and prevention of states including atherosclerosis of the coronary arteries causing coronary artery disease, myocardial infarction, coronary thrombosis, and angina pectoris;

atherosclerosis of the arteries supplying the central nervous system causing strokes and transient cerebral ischemia; atherosclerosis of the peripheral circulation causing intermittent claudication and gangrene; atherosclerosis of an artery of the splanchnic circulation causing mesenteric ischemia; and renal artery stenosis.

Thus, the composition of the invention is further suitable for use in the treatment or prevention of at least one disease or disorder associated with one or more of increased serum lipid triglyceride concentrations, serum cholesterol concentrations and serum total and LDL cholesterol concentrations and decreased HDL-cholesterol concentrations.

As used herein, such a disease or disorder associated with increased serum lipid triglyceride concentrations, serum cholesterol concentrations and serum total and LDL cholesterol concentrations and decreased HDL-cholesterol concentrations, involve abnormally high cholesterol levels (hypercholesterolemia), and/or high levels of LDL or triglycerides and/or lower concentrations of functional HDL, such as coronary heart disease or other forms of cardiovascular disease as well as diseases or disorders which involves atheroma development in arteries (i.e., atherosclerosis), such as hypocholesterolemia, peripheral vascular disease, diabetes and high blood pressure.

Oxidative stress has been also linked also to neuronal cell death that is associated with various neurodegenerative conditions. Neurodegenerative diseases are conditions in which cells of the brain and spinal cord are lost. Normally, neurodegeneration begins long before the patient experiences any symptoms. As brain cells are continuously exposed to reactive oxygen species generated by oxidative metabolism, oxidative stress is also one of the predisposing factors in adult neurological disorders and has been implicated in the pathogenesis of some of these disorders such as Parkinson's disease.

The extract or composition of the invention is also used for the treatment or prevention of at least one neurodegenerative associated disease or disorder.

The 'neurodegenerative diseases or disorders', in the context of the present invention, refer to one or more condition in which cells of the brain and spinal cord are lost as a result of deterioration of neurons or their myelin sheath which over time leads to dysfunction and disabilities resulting from this. Thus, the neurodegenerative diseases or disorders are those relating to conditions causing problems with movements, such as ataxia, and also to conditions affecting memory and related to dementia. Some non-limiting examples of neurodegenerative diseases or disorders include alcoholism, Alexander's disease, Alper's disease, Alzheimer's disease, amyotrophic lateral sclerosis (Lou Gehrig's Disease), ataxia telangiectasia, Batten disease (also known as Spielmeyer-Vogt-Sjögren-Batten disease), bovine spongiform encephalopathy (BSE), canavan disease, cerebral palsy, cockayne syndrome, corticobasal degeneration, Creutzfeldt-Jakob disease, frontotemporal lobar degeneration, Huntington's disease, HIV-associated dementia, Kennedy's disease, Krabbe's disease, lewy body dementia, neuroborreliosis, Machado-Joseph disease (spinocerebellar ataxia type 3), multiple system atrophy, multiple sclerosis, narcolepsy, Niemann Pick disease, Parkinson's disease, Pelizaeus-Merzbacher disease, Pick's disease, primary lateral sclerosis, prion diseases, progressive supranuclear palsy, Refsum's disease, Sandhoffs disease, childer's disease, subacute combined degeneration of spinal cord secondary to pernicious anaemia, spinocerebellar ataxia, spinal muscular atrophy, Steele-Richardson-Olszewski disease, and tabes dorsalis.

In still yet another one of its aspects the present invention provides a method for the treatment or prevention of at least one disease or disorder associated with oxidative stress damage in a mammal, comprising administering to said mammal an effective amount of an extract according to the invention or a pharmaceutical composition comprising thereof.

In an additional aspect of the present invention there is provided a method for the treatment or prevention of at least one disease or disorder associated with one or more of increased serum lipid triglyceride concentrations, serum cholesterol concentrations and serum total and LDL cholesterol concentrations and decreased HDL-cholesterol concentrations in a mammal, comprising administering to said mammal an effective amount of an extract according to the invention or a pharmaceutical composition comprising thereof.

In a further one of its aspects the present invention provides a method for the treatment or prevention of at least one neurodegenerative associated disease or disorder in a mammal comprising administering to said mammal an effective amount of an extract according to the invention or a pharmaceutical composition comprising thereof.

In yet a further aspect, the present invention provides an antioxidant comprising the extract of the invention.

In still yet a further aspect, the present invention provides a cholesterol-reducing agent comprising the extract of the invention.

Within the scope of the present invention, the term 'treating and/or preventing' refers to the administering of a therapeutic amount of the composition of the present invention which is effective to ameliorate undesired symptoms associated with a disease, to prevent the manifestation of such symptoms before they occur, to slow down the progression of the disease, slow down the deterioration of symptoms, to enhance the onset of remission period, slow down the irreversible damage caused in the progressive chronic stage of the disease, to delay the onset of said progressive stage, to lessen the severity or cure the disease, to improve survival rate or more rapid recovery, or to prevent the disease form occurring or a combination of two or more of the above.

An extract or a composition of the invention may be administered by any method known to a person skilled in the art. Typically, the administration of an extract or a pharmaceutical composition comprising thereof is of an effective amount of the extract(s) comprised in the composition. The 'effective amount' for purposes herein is determined by such considerations as may be known in the art. The amount must be effective to achieve the desired therapeutic effect as described above, depending, inter alia, on the type and severity of the disease to be treated and the treatment regime. The effective amount is typically determined in appropriately designed clinical trials (e.g., dose range studies) and the person versed in the art will know how to properly conduct such trials in order to determine the effective amount. As generally known, an effective amount depends on a variety of factors including the affinity of the ligand to the receptor, its distribution profile within the body, a variety of pharmacological parameters such as half-life in the body, on undesired side effects, if any, on factors such as age and gender, etc.

The extract of the invention may also be used to prepare a composition for use in a variety of non-pharmaceutical applications. In some embodiments, the composition is an antioxidant composition for use as a preservative for a great variety of applications in the food industry, cosmetic industry, therapeutics, etc., and for the inhibition of copper ion-induced LDL oxidation in vitro or in vivo.

The extract disclosed herein may additionally be used as a nutritional supplement or as an active component of such supplement. In some embodiments, the supplement is suitable for consumption by both humans and non-human animals, for the management of well-being, and treatment and prevention of conditions and disorders associated with oxidative damage.

Within the context of the present invention, the nutritional supplement, depending on its nature and physical form, e.g., lipophilic or hydrophilic in nature, may further comprise one or more of emulsifiers, stabilizers, antioxidants and other additives. Use is made of emulsifiers compatible in food, such as phospholipids, for example lecithin, polyoxyethylene sorbitan mono- or tristearate, monolaurate, monopalmitate, mono- or trioleate, a mono- or diglyceride. These emulsifiers, stabilizers, antioxidants and additives may be added to the extract of the invention according to the final use of said extract.

The nutritional supplement disclosed herein may also contain synthetic or natural bioactives such as amino acids, fatty acids, vitamins, minerals, polyphenols, etc., that can be added either by dry or by wet mixing to said composition before pasteurization and/or drying.

In some embodiments, the nutritional supplement is a nutritional complete formula, a dairy product, a chilled or shelf stable beverage, a mineral or purified water, a liquid drink, a soup, a dietary supplement, a meal replacement, a nutritional bar, a confectionery, a milk or a fermented milk product, a yoghurt, a milk based powder, an enteral nutrition product, an infant formula, an infant nutritional product, a cereal product or a fermented cereal based product, an ice-cream, a chocolate, coffee, a culinary product such as mayonnaise, tomato puree or salad dressings or a pet food. According to these embodiments, the extract of the invention may be dispersed in the foods or drinks so as to have a daily intake in bioactive nutrients, which depends mainly on the type of food in which the extract is dispersed, the desired effect and target tissue. The amount of the food supplement to be consumed by the individual to obtain a beneficial effect will also depend upon one or more various factors such as the type of supplement and/or food and age and weight of consumer.

The nutritional supplement for oral administration may be in capsules, gelatin capsules, soft capsules, tablets, sugar-coated tablets, pills, pastes or pastilles, gums, or drinkable solutions or emulsions, syrup or a gel, with a dose of about 0.1 to 100% of the extract of the invention, which can then be taken directly with water or by any other known means. This supplement may also include a sweetener, a stabilizer, an antioxidant, an additive, a flavoring or a colorant.

It is appreciated that certain features of the invention, which are, for clarity, described in the context of separate embodiments, may also be provided in combination in a single embodiment. Conversely, various features of the invention, which are, for brevity, described in the context of a single embodiment, may also be provided separately or in any suitable sub-combination or as suitable in any other described embodiment of the invention. Certain features described in the context of various embodiments are not to be considered essential features of those embodiments, unless the embodiment is inoperative without those elements.

As used herein, the process, the extract or compositions of the invention may include additional steps or ingredients or parts, only if the additional steps, ingredients, or parts do not alter the basic and novel characteristics of the claimed process, extract and compositions. As used herein, the singular form "a", "an" and "the" include plural references unless the context clearly dictates otherwise.

BRIEF DESCRIPTION OF THE DRAWINGS

In order to understand the invention and to see how it may be carried out in practice, embodiments will now be described, by way of non-limiting example only, with reference to the accompanying drawings, in which:

FIGS. 3A and 3B show the free radical scavenging capacity of marula juice extracts at 1 µL/ml (FIG. 3A) and 2 µL/ml (FIG. 3B).

FIG. 4B—Lipid peroxidases).

FIG. 5B—Lipid peroxidases).

FIG. 14B—FRAP assay).

DETAILED DESCRIPTION OF THE INVENTION

Figure 1:
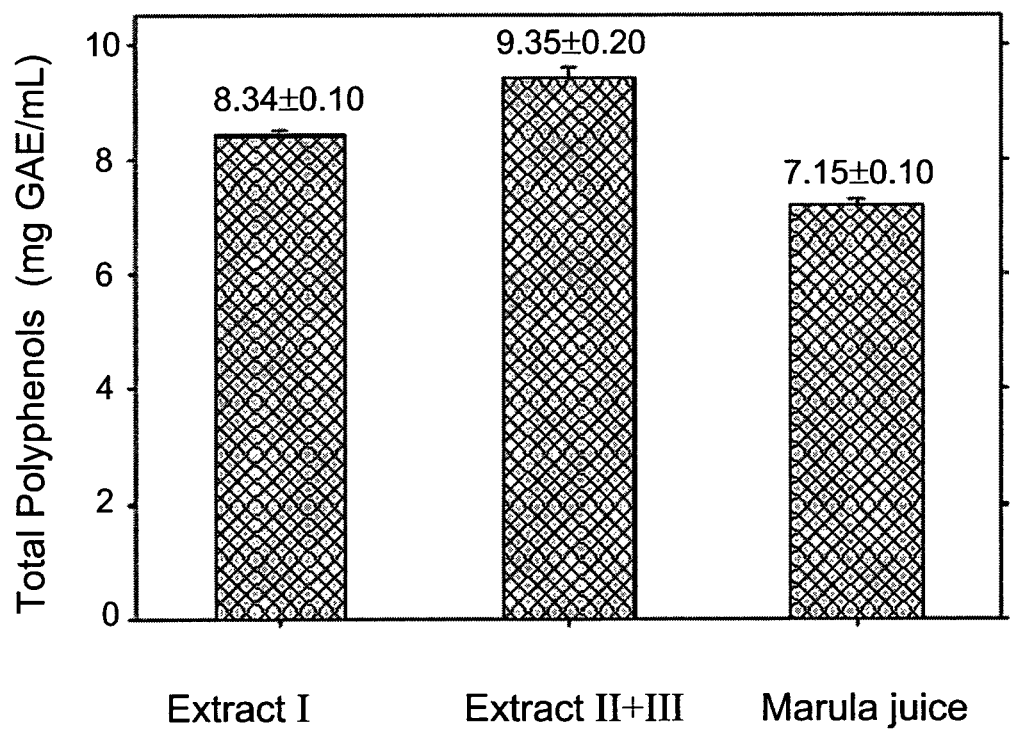
FIG. 1 shows polyphenol concentrations in marula juice extracts.
Figure 2A:
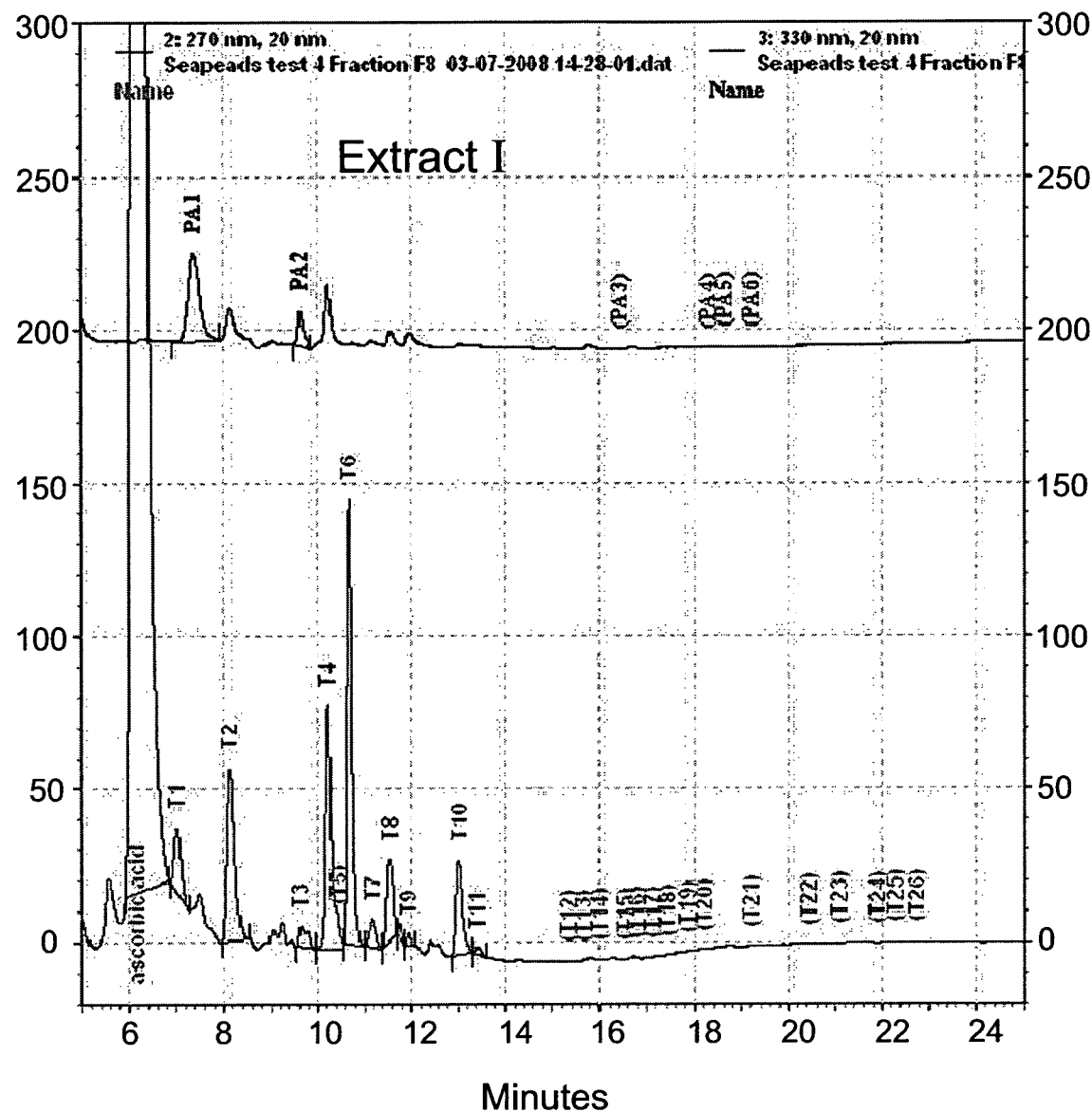
FIGS. 2A-D shows HPLC chromatograms, at 270 (green) and 330 (blue) nm, obtained in methanol of extract I (FIG. 2A), extract II (FIG. 2B), extract III (FIG. 2C) and marula juice (FIG. 2D). Peaks corresponding to tannins (T) and phenolic acids (PA) are numbered.
Figure 2B:
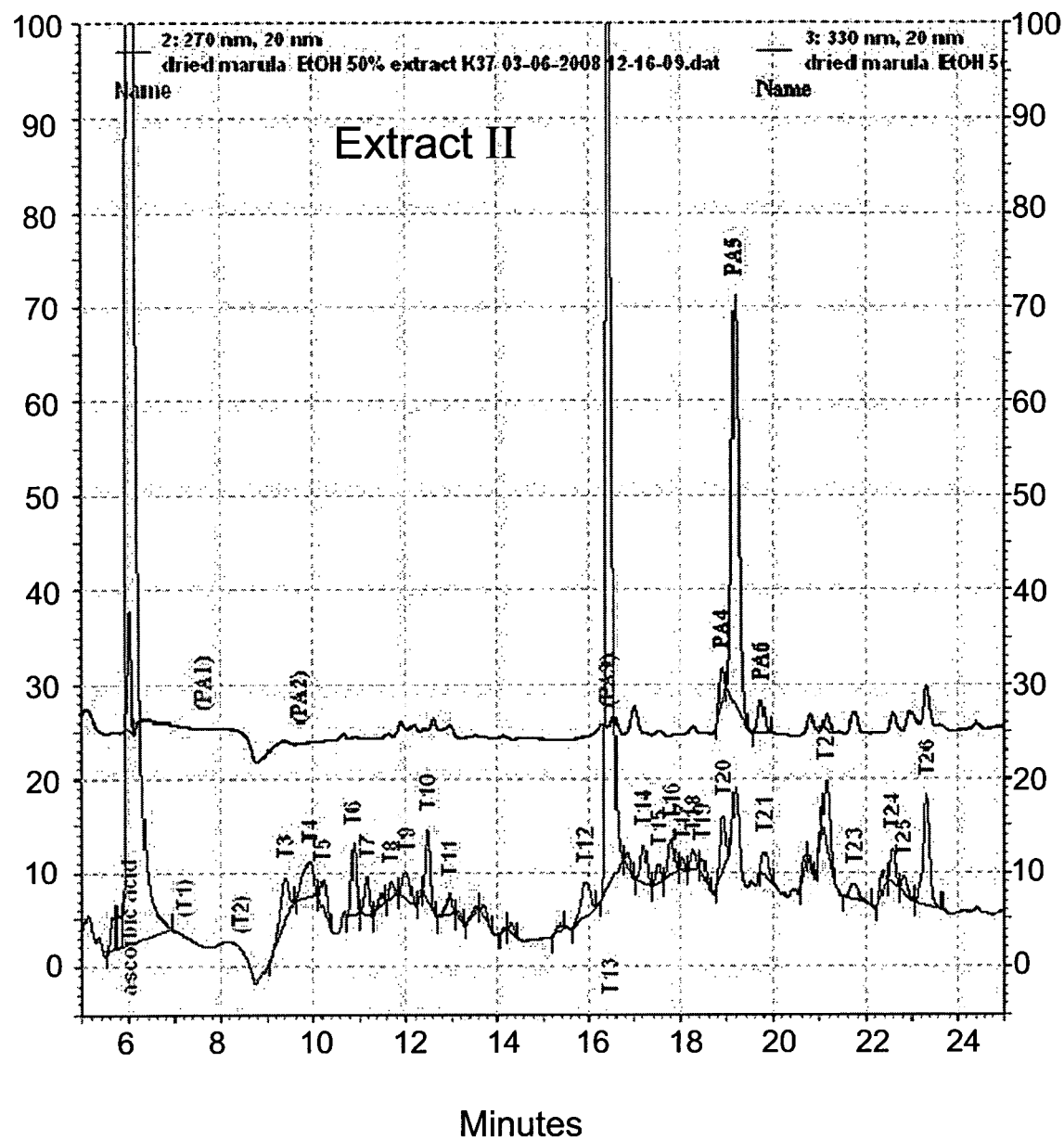
Figure 2C:
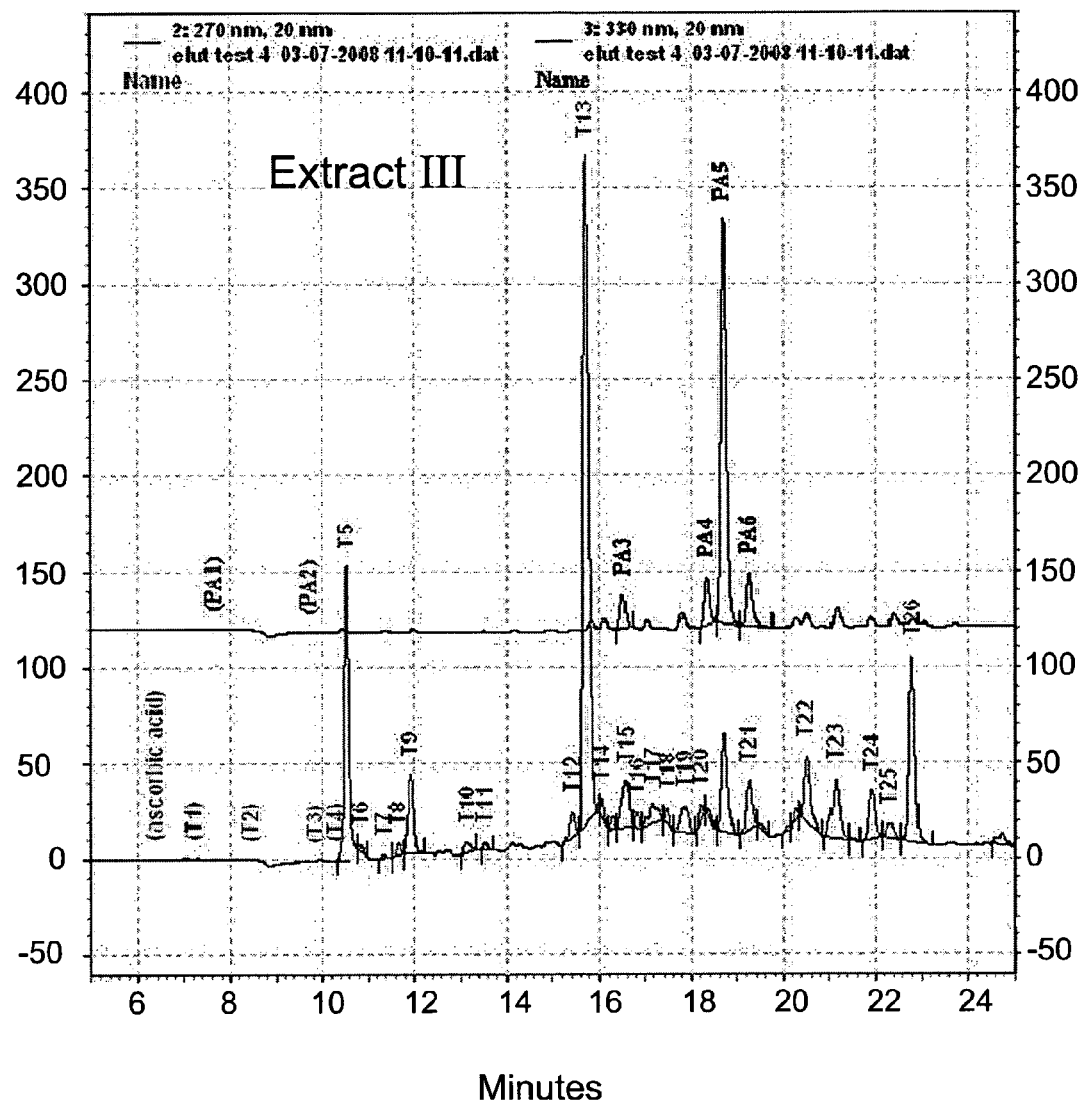
Figure 2D:
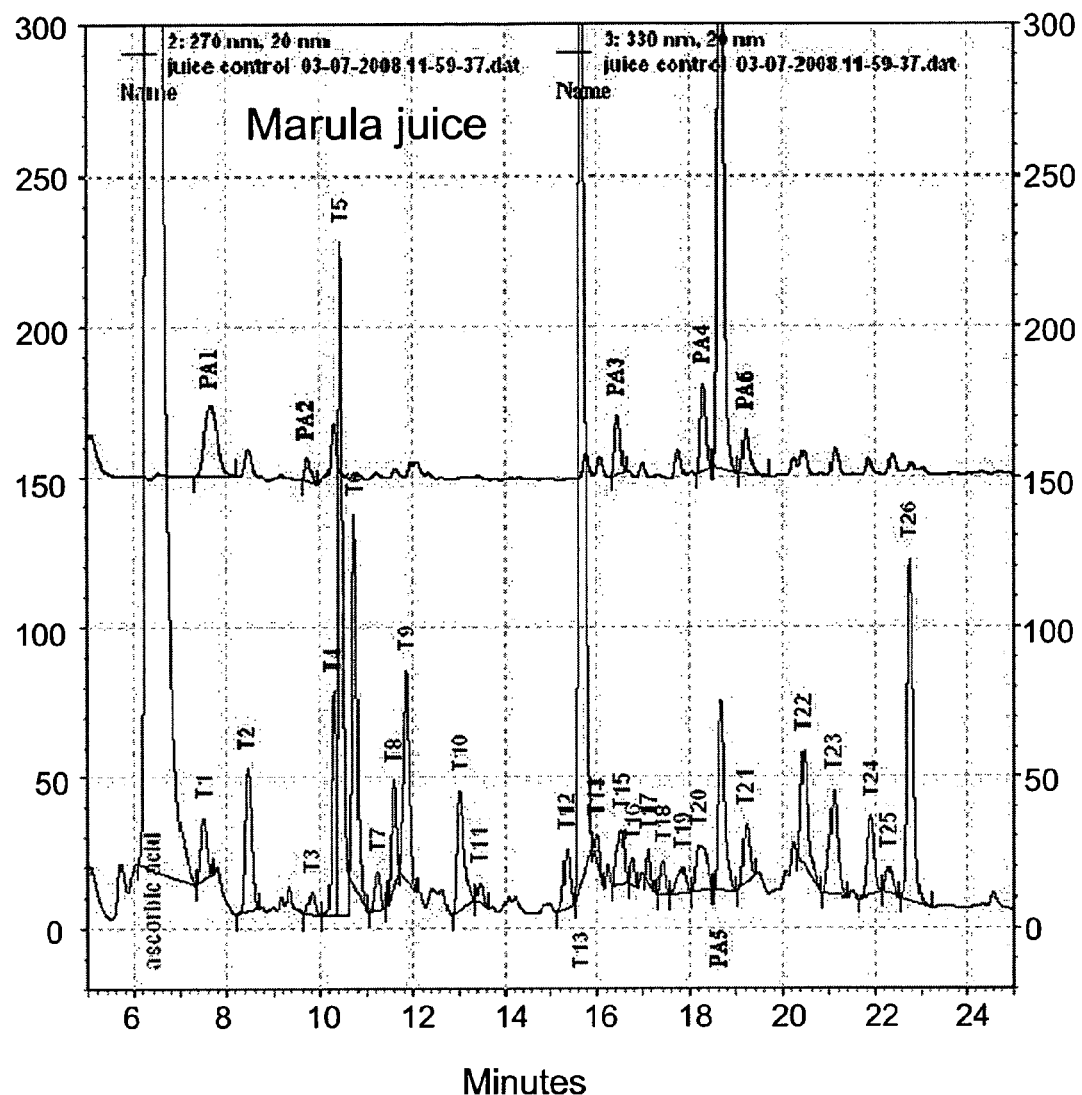

Various embodiments and aspects of the present invention as delineated hereinabove and as claimed in the claims section below find experimental support in the following examples.

1. Drying of Marula Juice

Marula fruits were collected from the ground within 10 days from the time the fruit fell off the trees and were than squeezed by a hydraulic press under 35 bar (Enorossi olive press model 250). Juice was collected and stored frozen at −20° C. for different periods up to 3 years. Immediately before drying, juice was defrosted and pored over aluminum foil trays, to form a uniform layer, 0.7-cm thick. Trays containing the juice were placed in a vacuum oven (Tuttnauer, oven dry sterilizer model 11-900), set at 57° C. and −760 mm mercury, for a period of 3 days. After drying, bearing approximately 1% moisture, the solid substance was milled, to yield a powder, readily soluble in water. The powder was kept in a desiccator, at room temperature, for several months.

2. Marula Extract Preparations

A. Ethanolic Extract (Referred to Herein as 'Extract I')

For preparing extract I, 15 grams of dried marula juice were crushed to powder, suspended in 50 ml of 50% ethanol and placed on a shaker for 20 min. The suspension was centrifuged and the supernatant transferred to a round flask. The step was repeated with additional 25 ml of 50% ethanol. The two supernatants were combined and the ethanol and some of the water were removed using a rotary evaporator. The final 30 ml aqueous solution had a FRAP (ferric reducing antioxidant power) antioxidative capacity of 1,390 mg vitamin C equivalents per 100 ml (3-fold the antioxidative capacity compared to the 460 mg vitamin C equivalents per 100 ml measured in the original juice). Extract I may be reconstituted in water.

B. Polyphenolic-Depleted Fraction (Referred to Herein as 'Extract II'):

For the preparation of extract II, whole marula juice was passed through 8 layers of cheesecloth and centrifuged to remove fruit tissue debris. 200 ml clear juice was applied to 20 ml Sepabeads column at a flow rate of 0.4 ml/min. 12-ml fractions were collected. Fractions containing the same total soluble solids concentration (TSS) as the clear juice (12.9%) were combined. The FRAP antioxidative activity measured in this fraction was 379 mg vitamin C equivalents per 100 ml, approximately 83% of that measured in the clear juice applied to the column.

C. Polyphenolic Fraction (Referred to Herein as 'Extract III').

For the preparation of extract III, batch-wise extraction was used to free the polyphenols from the column beads described above. The beads were transferred to a wide bottom glass flask and mixed rigorously with 85% ethanol solution. The ethanolic solution was recovered and the step was repeated until the extraction solution was colorless. The collected ethanolic solutions were combined, placed in a round flask and evaporated to dryness with a rotary evaporator. The dry film was dissolved in 1 ml water. The resulting product had a FRAP activity of 5,735 mg vitamin C equivalents per 100 ml, being ~12 folds the activity measured in the original juice.

For obtaining a polyphenolic enriched marula drink, 15 ml of polyphenolic-depleted juice fraction (extract II) was mixed with the isolated polyphenolic fraction (extract III); water was added to a final volume of 25 ml marula drink (comprising the herein described extracts II and III) with a FRAP antioxidative activity of 446 mg vitamin C equivalents per 100 ml, of which, 50% were contributed by vitamin C and 50% by polyphenols, compared to ~75% and 25%, respectively, in the original juice.

Total polyphenols were determined spectrophotometrically by the method of Singleton modified for small volumes [Singleton V L, et al, Am. J. Emology and Viticulture 16:144-158, 1965]. Gallic acid (GA) served as a standard. GA stock solution was prepared in water at a concentration of 2 mM. Volumes of 10, 20, 40 and 60 microliter were used for the standard curve. Results were then expressed as GA equivalents (GAE). Occasionally, pyrogallol replaced GA as a standard.

3. In Vitro Methods

FIG. 1 shows the total polyphenol concentration in each of the filtered marula juice, ethanolic extract of dried marula juice (extract I) and a product obtained by combining the herein described extracts II and III. The total concentration was 7.15, 8.34 and 9.35 mg of gallic acid equivalents (GAE)/ml, respectively.

FIG. 2 presents the HPLC chromatograms of marula juice and juice extracts. Each juice extract was washed (1:3) with 80% methanol supplemented with 2 mM NaF to extract the antioxidants. The suspension was centrifuged and the supernatant was filtered through a 0.45 µm filter before injection. Samples of 20 µL were analyzed using the LaChrom Merck Hitachi HPLC system, consisting of Pump L7100, Column oven L7350 (set at 28° C.), Mixer-degasser L-7614 and Manual Injector Rheodyne, coupled with Multiwavelength Detector (Jasco MD-2010 Plus), interface (Jasco LC-Net II/ADC) and scientific software (EZChrom Elite Client/Server version 3.1.6 build 3.1.6.2433). An end-capped Purospher®Star RP-18 column (250×4 mm LichroCART® cartridge, 5 µm particle size) with end-capped Lichrospher®100 RP-18 guard column (4×4 mm LichroCART® cartridge, 5 µm particle size) were used.

Column ending was connected to a fraction collector (Pharmacia Fine Chemicals, FRAC-100). The mobile phases consisted of (A) phosphoric acid (0.1%), pH 2.4, and (B) methanol; the elution gradient was set to go from 0 to 100% methanol in 30 minutes. The flow rate was 0.6 mL min$^{-1}$.

Vitamin C concentration was evaluated from the area under the corresponding chromatogram peaks using HPLC-grade vitamin C (Fluka) for calibration. Methanol was HPLC grade (LiChrosolv Merck); water was purified and filtered using known procedures; phosphoric acid (Frutarom) and NaF (Sigma) were of analytical grade. Phenolics standard library was constructed using catechin, chlorogenic-, caffeic- and tannic-acid from Sigma, and 2-hydroxybenzoic (salicylic) acid, quercetin-3-β-glucoside and ellagic acid from Fluka.

As the HPLC chromatograms indicate each extracts I, II, III had a unique composition with respect to phenolic compounds [phenolic acids (PA) and tannins (T)] and vitamin C. The three extracts differed significantly in their antioxidant composition compared to the original juice.

The free radical-scavenging capacity of the marula juice products was analyzed also by the DPPH assay [Malterud K M, Farbort T L, Huse ACE, Bredo Sund R. Antioxidant and radical scavenging effects of arthraquinones and anthorones. Pharmacology. 1993: 47: 77-85]. DPPH (1,1-diphenyl-2-picryl-hydrazyl) is a free radical generating substance that is widely used to monitor the free radical scavenging abilities (the ability of a compound to donate an electron) of various antioxidants. The DPPH radical has a deep violet color due to its impaired electron, and radical scavenging can be followed spectrophotometrically by the loss of absorbance at 517 nm, as the pale yellow non-radical form is produced.

Marula juice product aliquots (1.0 µl) were mixed with 1 mL of 0.1 mmol DPPH/L in ethanol, and the change in optical density at 517 nm was continuously monitored. The capacity of marula juice extracts to scavenge free radicals was compared to the free radical scavenging capacity of filtered marula juice (FIGS. 3A and 3B).

At a concentration of 1.0 µl/ml, filtered marula juice induced a 30% decrease in the optical density at 517 nm, whereas a product obtained by combining the herein described extracts II and III (e.g., marula juice enriched with high levels of polyphenols) induced a 21% decrease in the optical density at 517 nm. The most remarkable radical scavenging capacity was exhibited by extract I, which induced a 54% decrease in the optical density at 517 nm (FIG. 3A). At higher concentrations (2.0 µl/ml), filtered and centrifuged marula juice induced a 60% decrease in the optical density at 517 nm. Similarly, the product obtained by combining the herein described extracts II and III induced a 43% decrease in the optical density at 517 nm, and the most remarkable radical scavenging capacity was again exhibited by extract I, which induced a 89% decrease in the optical density at 517 nm (FIG. 3B).

LDL was isolated from plasma derived from healthy normolipidemic volunteers, by discontinuous density gradient ultra-centrifugation [Aviram, M. (1983) Plasma lipoprotein separation by discontinuous density gradient ultracentrifugation in hyperlipoproteinemic patients. Biochem. Med. 30, 111-118]. The LDL was washed at d=1.063 g/ml, dialyzed against 150 mmol/L NaCl, 1 mmol/L $Na_2EDTA$ (pH 7.4) at 4° C. The LDL was then sterilized by filtration (0.45 µM), kept under nitrogen in the dark at 4° C. and used within 2 weeks. The LDL protein concentration was determined with the Folin Phenol reagent. Prior to oxidation, LDL was dialyzed against EDTA-free, phosphate buffered saline (PBS) solution, pH 7.4, and at 4° C.

LDL (100 µg of protein/mL) was incubated for ten minutes at room temperature with increasing concentrations of marula juice extracts. Then, 5 µmol/L of $CuSO_4$ was added and the tubes were incubated for 2 hours at 37° C. At the end of incubation, the extent of LDL oxidation was determined by measuring the generated amount of thiobarbituric acid reactive substances (TBARS) and of lipid peroxides [Aviram M, Vaya J. Markers for low-density lipoprotein oxidation. Methods Enzymol. 2001; 335:244-56; and Buege J. A., Aust S. D. Microsomal lipid peroxidation. Methods Enzymol. 52: 302-310 (1978)]. The lipid peroxide (PD) test analyzes lipid peroxide formation by their capacity to convert iodide to iodine after incubation for 18 hours at 25° C., as measured spectrophotometrically at 365 nm [G. Jurgens. A spectrophotometric assay for lipid peroxides in serum lipoproteins using a commercially available reagent. J. Lipid Res. 30: 627-630, 1986].

Figure 4B:
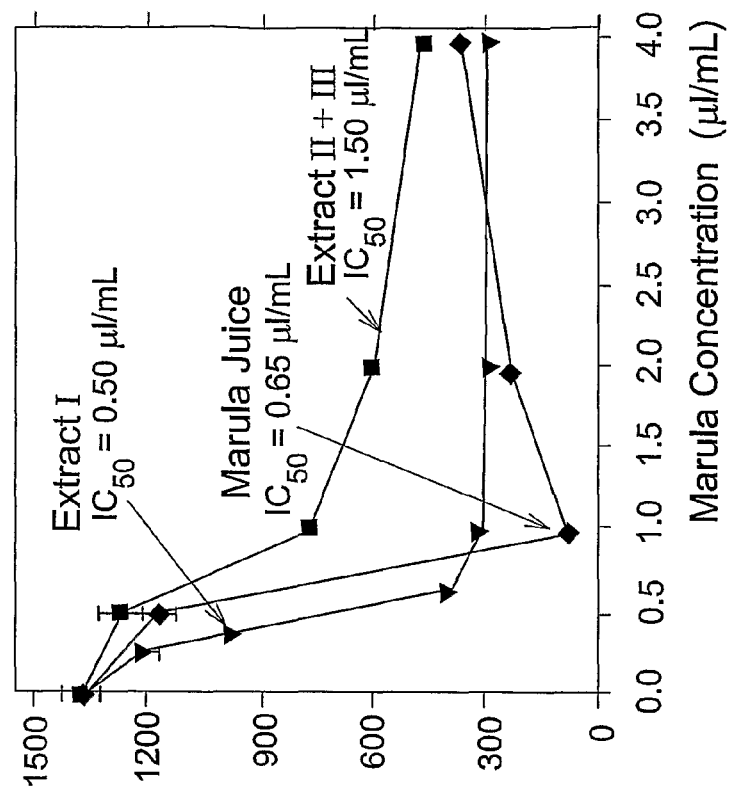
FIGS. 4A and 4B show the copper ion-induced LDL oxidation inhibition capacity of the extracts in comparison to the marula juice (FIG. 4A—TBARS.
Figure 4A:
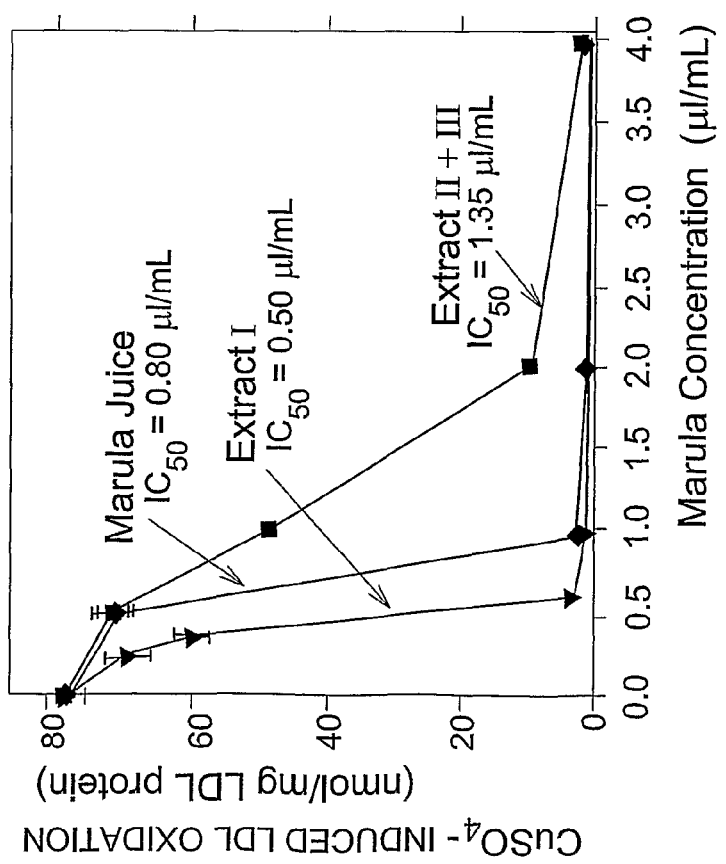
Figure 5A:
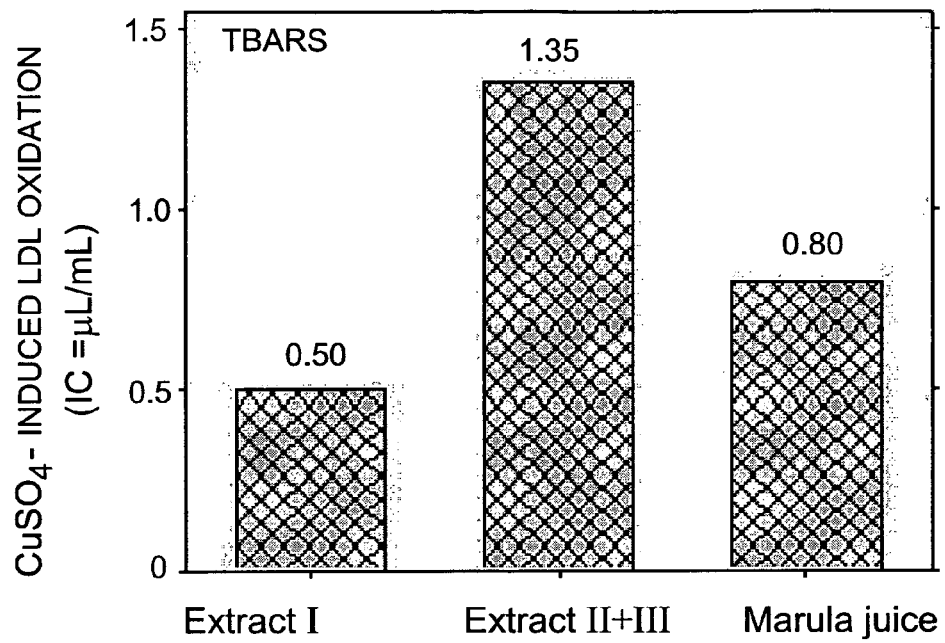
FIGS. 5A and 5B show copper ion-induced LDL oxidation inhibition capacity of the extracts in comparison to the marula juice: $IC_{50}$ analysis (FIG. 5A—TBARS.
Figure 5B:
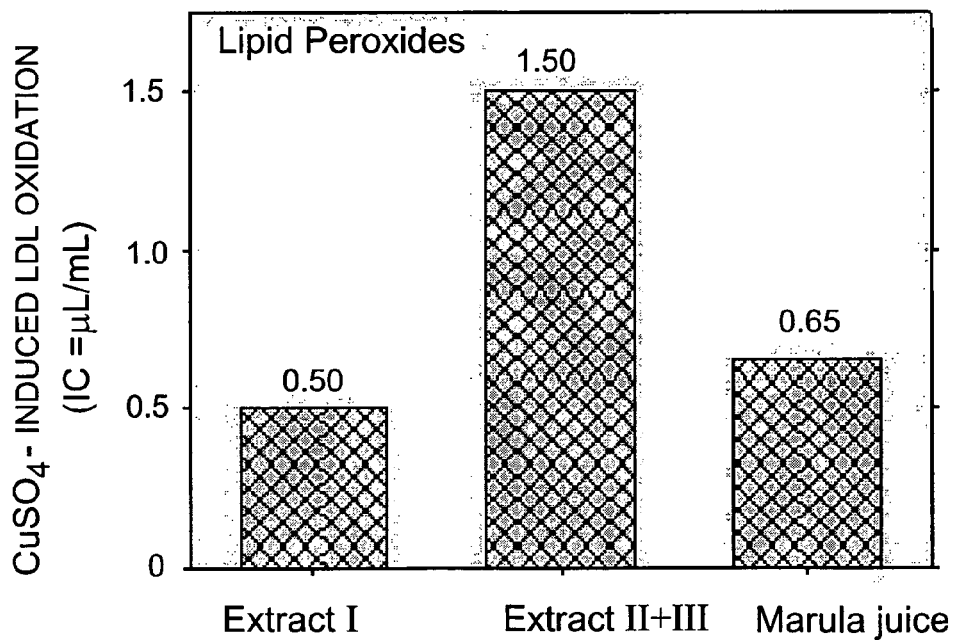

LDL oxidation was measured as TBARS (FIG. 4A) or as lipid peroxides formation (FIG. 4B). The addition of increasing concentrations of marula juice extracts inhibited copper ion-induced LDL oxidation in a dose-dependent manner. The $IC_{50}$ (inhibition of LDL oxidation by 50%) value for filtered and centrifuged marula juice was 0.80 µl/mL for the TBARS (FIG. 5A) and 0.65 µl/mL for the lipid peroxides (FIG. 5B) formation. Somewhat lower results were obtained for extract I (0.50 µl/mL for both TBARS and the lipid peroxides formation). On the contrary, the $IC_{50}$ value for a product obtained by combining the herein described extracts II and III was the highest (1.35 and 1.50 for the TBARS and for the lipid peroxides, respectively).

J-774A.1 macrophages were preincubated with 10 and 30 µg GAE equivalents/ml of marula juice products, and then the cells were analyzed for their atherogenicity, which was evaluated as macrophage oxidative status, macrophage uptake of lipoproteins, HDL-mediated cholesterol efflux, and cholesterol biosynthesis Macrophage oxidative status was determined by the flow-cytometric assay with dichlorofluorescin-diacetate (DCFH-DA). DCFH-DA is a nonpolar dye that diffuses into cells. In the cells it is hydrolyzed into the nonfluorescent derivate 2',7'-dichlorofluorescin (DCFH), which is polar and trapped within the cells. Under oxidative stress, DCFH is oxidized to DCF, which is a fluorescent compound. J774 A.1 ($2\times10^6$) macrophages were incubated with $2.5\times10^{-5}$ mol/L DCFH-DA for 30 minutes at 37° C. Reaction was stopped by washes with PBS at 4° C. Cellular fluorescence was determined with a flow cytometry apparatus (FACS-SCAN, Becton Dickinson, San Jose, Calif., USA). Measurements were done at 510 to 540 nm after excitation of cells at 488 nm with an argon ion laser.

Figure 6:
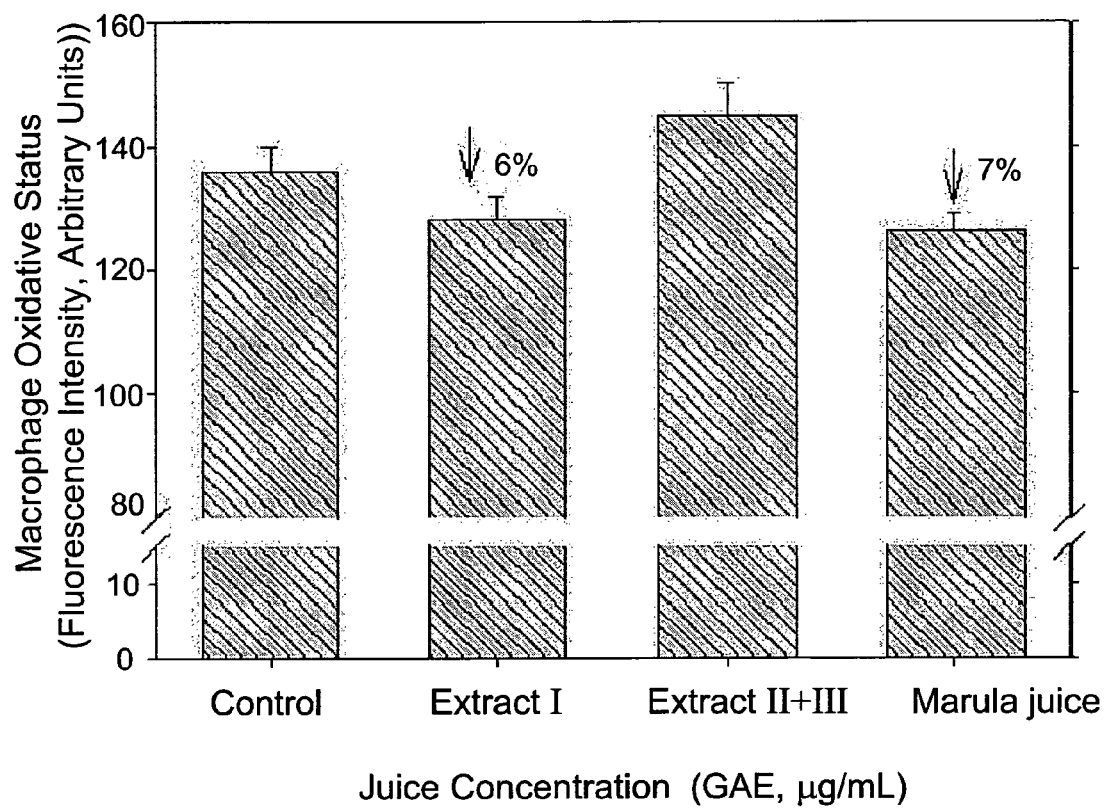
FIG. 6 demonstrates the ability to reduce macrophage oxidative stress.

Incubation of J-774A.1 macrophages for 18 hours at 37° C. with extract I and filtered marula juice, reduced cellular oxidative stress, as measured by the DCFH assay, by 6% and 7%, respectively. The product obtained by combining the herein described extracts II and III had no effect on macrophage oxidative stress status (FIG. 6).

LDL (1 mg/mL) was incubated for 18 hours at 37° C. with 5 µmol/L freshly prepared $CuSO_4$. Oxidation was terminated by refrigeration at 4° C. The extent of LDL oxidation was determined by the TBARS assay.

LDL and Ox-LDL were conjugated to fluoroisothiocyanate (FITC) for cellular uptake studies. Lipoproteins (2.5 mg protein/ml) were dialyzed overnight at 4° C. against several changes of borate buffer containing 0.1 M borate, 25 mM sodium tetraborate, 75 mM NaCl, pH 8.6. Prior to conjugation (1 h), the pH of the dialysis buffer was altered to 9.4. Fluorescein isothiocyanate (FITC; Sigma-Aldrich) was dissolved in dimethyl formamide (Merck) and added drop wise to the lipoproteins solution to give a final concentration of 0.2 mg/ml and then incubated for 1 h at room temperature with stirring. FITC-conjugated lipoproteins were separated from unconjugated FITC by size exclusion chromatography over a PD-10 column (Amersham-Pharmacia Biotech), eluting with 10 mM phosphate buffer, pH 8.0. FITC-labeled lipoproteins (2 mg/ml) were used immediately in uptake studies.

J774A.1 macrophages were incubated at 37° C. for 3 hours with FITC-conjugated LDL or Ox-LDL at a final concentration of 25 µg of protein/ml. The uptake of the lipoprotein was determined by flow cytometry. Measurements of cellular fluorescence determined by FACS were done at 510 nm to 540 nm after excitation of the cells at 488 nm with an argon ion laser. Cellular fluorescence was measured in terms of mean fluorescence intensity (MFI).

Figure 7:
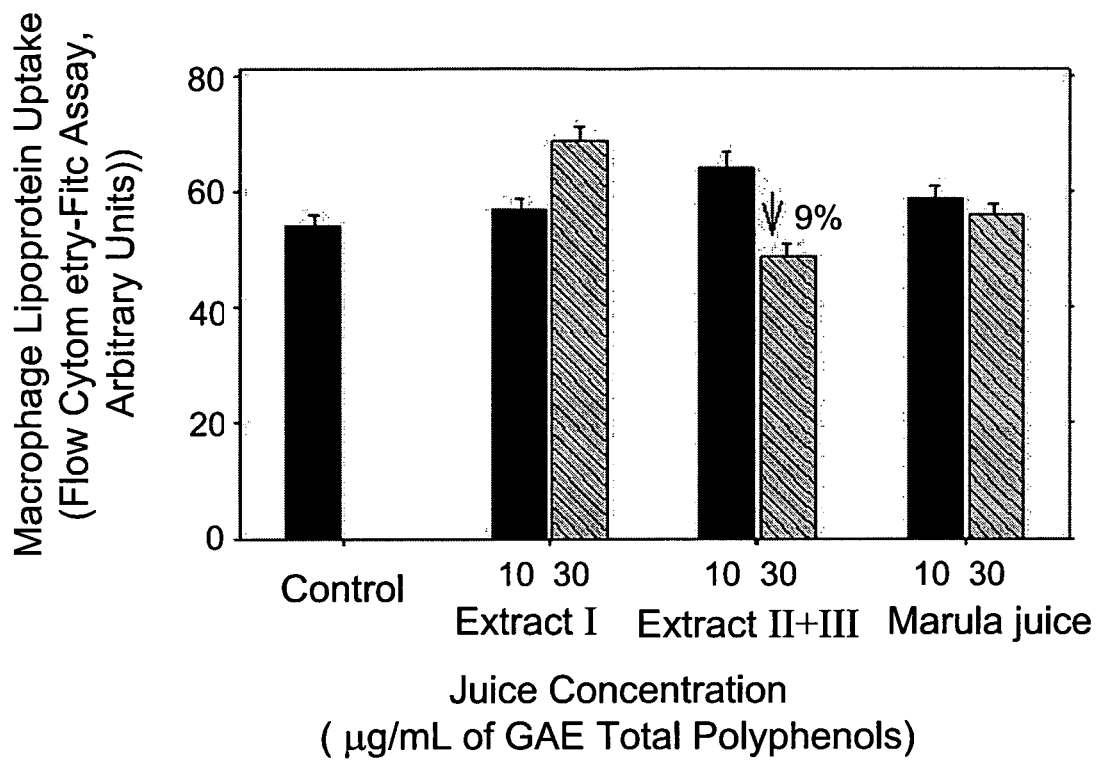
FIG. 7 shows the effect of marula juice extracts on LDL uptake by macrophages.
Figure 8:
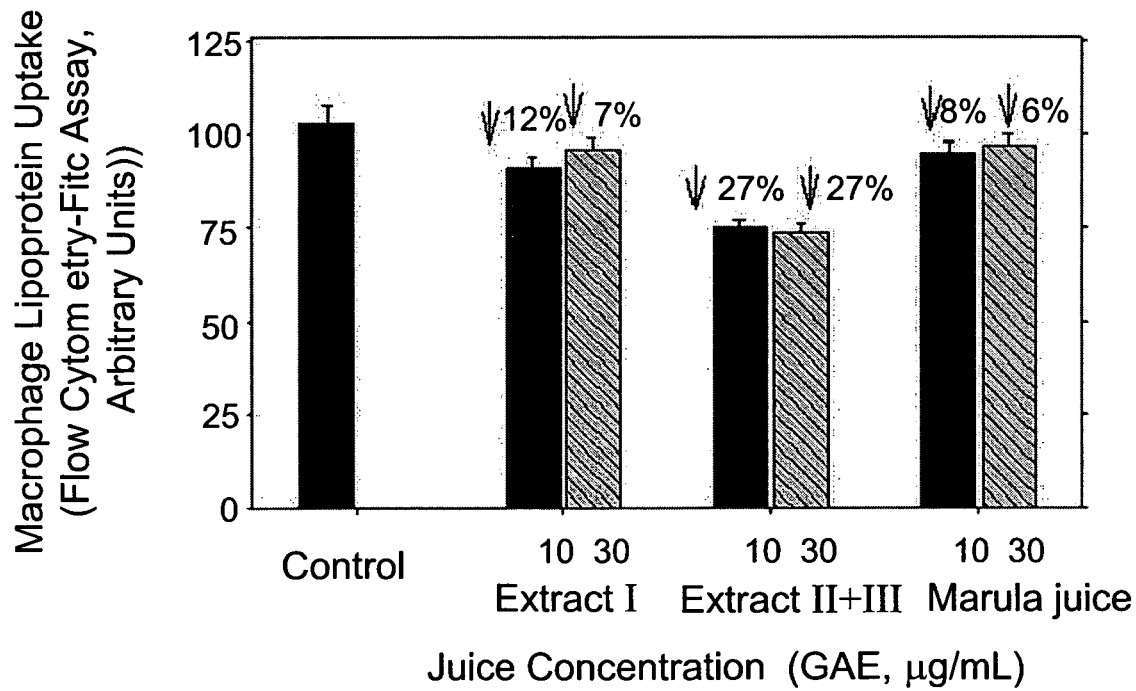
FIG. 8 shows the effect of marula juice extracts on Ox-LDL uptake by macrophages.

Incubation of J-774A.1 macrophages for 18 hours at 37° C. with marula juice products (10 µg/ml GAE) had no effect on LDL uptake by macrophages. At a higher concentration of 30 µg/ml GAE, only the product comprising the herein described extracts II and III reduced macrophage LDL uptake by 9% (FIG. 7). Incubation of J-774A.1 macrophages for 18 hours at 37° C. with extract I, a product obtained by combining the herein described extracts II and III and filtered marula juice, either at 10 µg/ml GAE or 30 µg/ml GAE, reduced macrophage uptake of Ox-LDL by 12% and 7% (extract I), by 27% (marula juice with high polyphenols content), and by 8% and 6% (filtered marula juice), respectively (FIG. 8).

Figure 9:
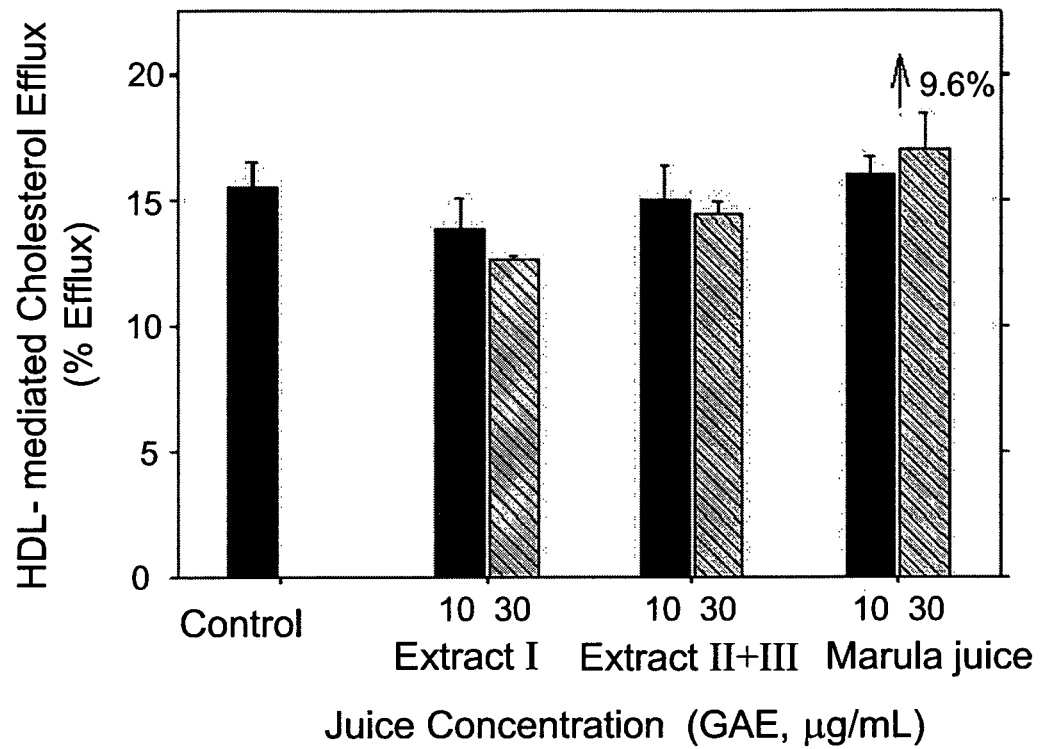
FIG. 9 shows the effect of marula juice extracts on HDL-mediated cholesterol efflux from macrophages.

J774 A.1 macrophages were incubated with [$^3$H]-labeled cholesterol (2 µCi/mL) for 1 hour at 37° C. followed by cell wash in ice-cold PBS (×3) and further incubation in the absence or presence of 100 µg of HDL protein/ml for 3 hours at 37° C. Cellular and medium [$^3$H]-labels were quantitated and HDL-mediated cholesterol efflux was calculated as the ratio of [$^3$H]-label in the medium/([$^3$H]-label in the medium+[$^3$H]-label in cells). Incubation of J-774 A.1 macrophages for 18 hours at 37° C. with filtered marula juice (10 µg/ml GAE) increased cholesterol efflux from macrophages to HDL by ~10%. However, all other marula juice products did not affect HDL-mediated cholesterol efflux at any concentration used (FIG. 9).

Figure 10:
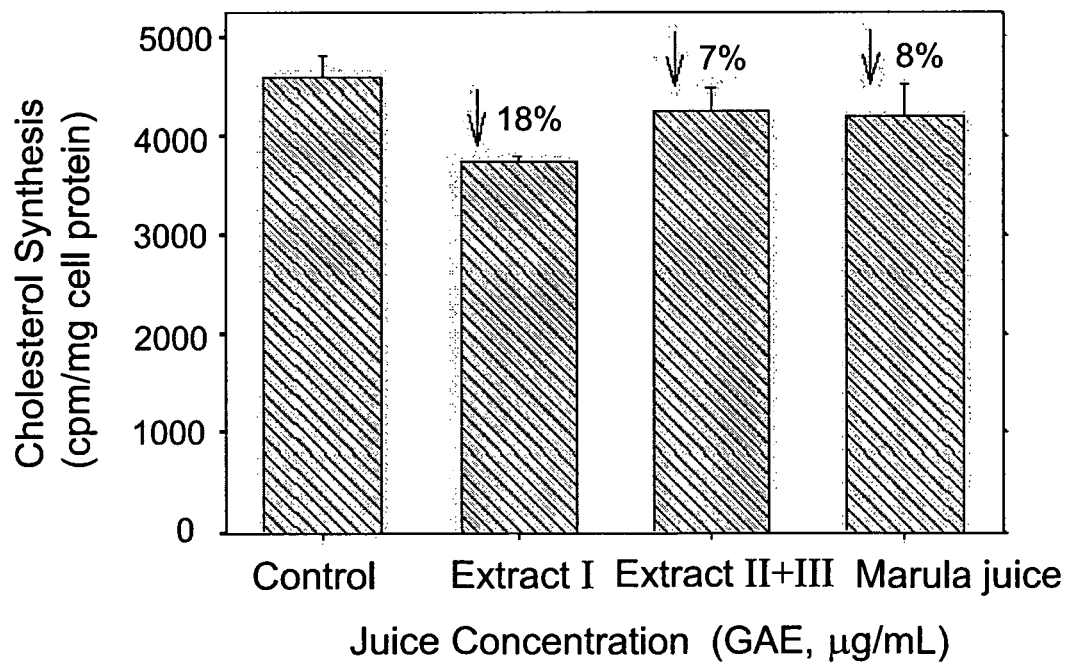
FIG. 10 shows the effect of marula juice extracts on cholesterol biosynthesis in macrophages.

J774 A.1 macrophages were incubated with [$^3$H] acetate, followed by cellular lipid extraction with hexane:isopropanol (3:2, v/v) and separation by thin layer chromatography (TLC) on silica gel plates. The spots of un-esterified cholesterol were visualized by iodine vapor, scraped into scintillation vials, and counted for radioactivity. Incubation of J-774 A.1 macrophages for 18 hours at 37° C. with extract I, a product obtained by combining the herein described extracts II and III and marula juice after filtration, all at concentration of 30 µg/ml GAE, reduced cholesterol biosynthesis in macrophages by 18%, 7%, and 8%, respectively (FIG. 10).

Newborn Wistar rats were obtained from Harlan Laboratories. Cultures of primary rat astrocytes were prepared from the cerebral cortices of 1-2 day-old neonatal Wistar rats. This procedure was approved by the Institutional Animal Care and Use committee. Astrocytes were plated in 24 well plates at 100,000 or 80,000 cells/0.5 ml/well, respectively. All experiments were performed in the presence of 2% serum (FCS). The original medium of the cells was aspirated off and fresh medium was added to the cells. Dilutions of $H_2O_2$ and marula juices in the growth medium were made freshly from stock solutions just prior to each experiment and were used immediately. Each treatment was performed in tetraplicates. The final concentration of $H_2O_2$ was 200 µM.

Neuronal Cells Culture Assays

Determination of cell viability—Cell viability was determined using a commercial colorimetric assay kit (supplied by Roche), based on the measurement of Lactate Dehydrogenase (LDH) activity released from the cytosol of damaged cells into the supernatant.

Figure 11:
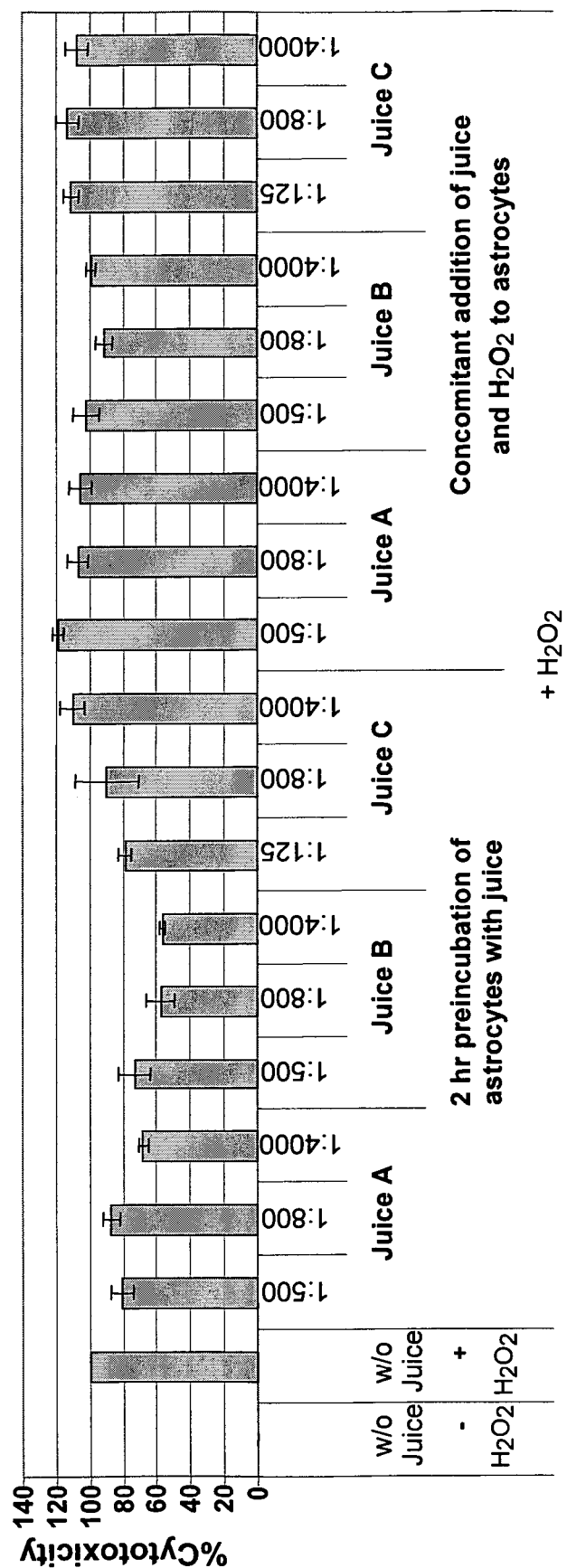
FIG. 11 shows the percentage of measured cytotoxicity for astrocytes treated with different concentrations of the juices/extracts, 2 hr before or concomitantly with $H_2O_2$ addition (Juice A–marula juice, Juice B–extract I, Juice C–extract II+extract III). The results are the mean±SD of an experiment performed in tetraplicates.

Protective effects of extracts—To determine the optimal conditions (in terms of time and dose) for the juices to exert their putative protective effect, cells were pretreated with different amounts of each juice product for different time periods and the products protective effects against oxidant stress generated by $H_2O_2$ were evaluated. Juices (at a dilution of 1:125, 1:500, 1:800 and 1:4000) were either concomitantly added with $H_2O_2$ or preincubated for two hr with the cells before its addition. The toxicity was monitored 20 hr later. FIG. 11 shows that at all concentrations tested and for all juice products, concomitant addition of the juices with $H_2O_2$ is not protective. However, preincubation for 2 hr with the cells prior to $H_2O_2$ addition resulted in protective effects of all juices, with extract I demonstrating the most effective protective activity when used at low concentrations (1:4000).

Experiments with marula extracts at low concentrations (dilutions 1:1000-1:8000)—The following experiments were performed at lower concentrations of the products (dilutions 1:1000-1:8000), being ~55-450 µg/100 ml vitamin C equivalents.

Figure 12:
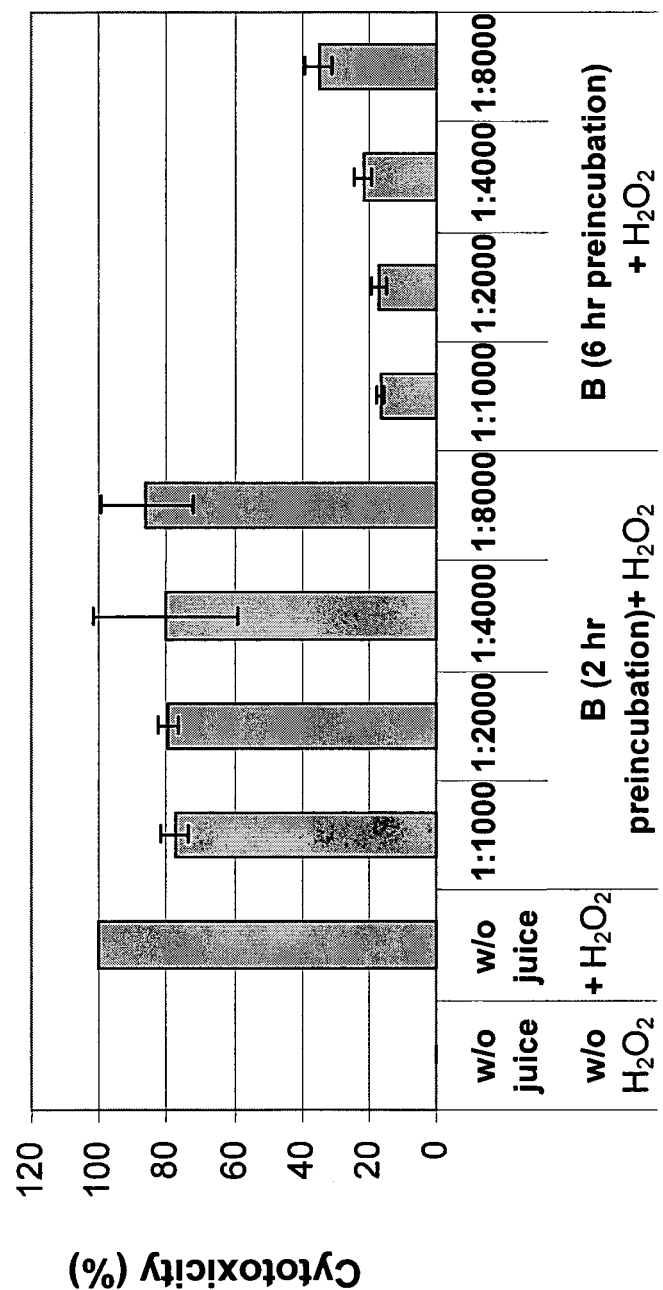
FIG. 12 shows the percentage of measured cytotoxicity for astrocytes preincubated with several concentrations of extract I (B) for 2 hrs or 6 hrs before the oxidative insult.

The effects of the preincubation period (2 hr vs. 6 hr) of cells with the juice products and of the product concentration (1:1000-1:8000) were tested. FIG. 12 shows that while 2 hr of preincubation with extract I caused only ~20% protection at all the tested concentrations, 6 hr of preincubation resulted in more than 80% protection.

Figure 13:
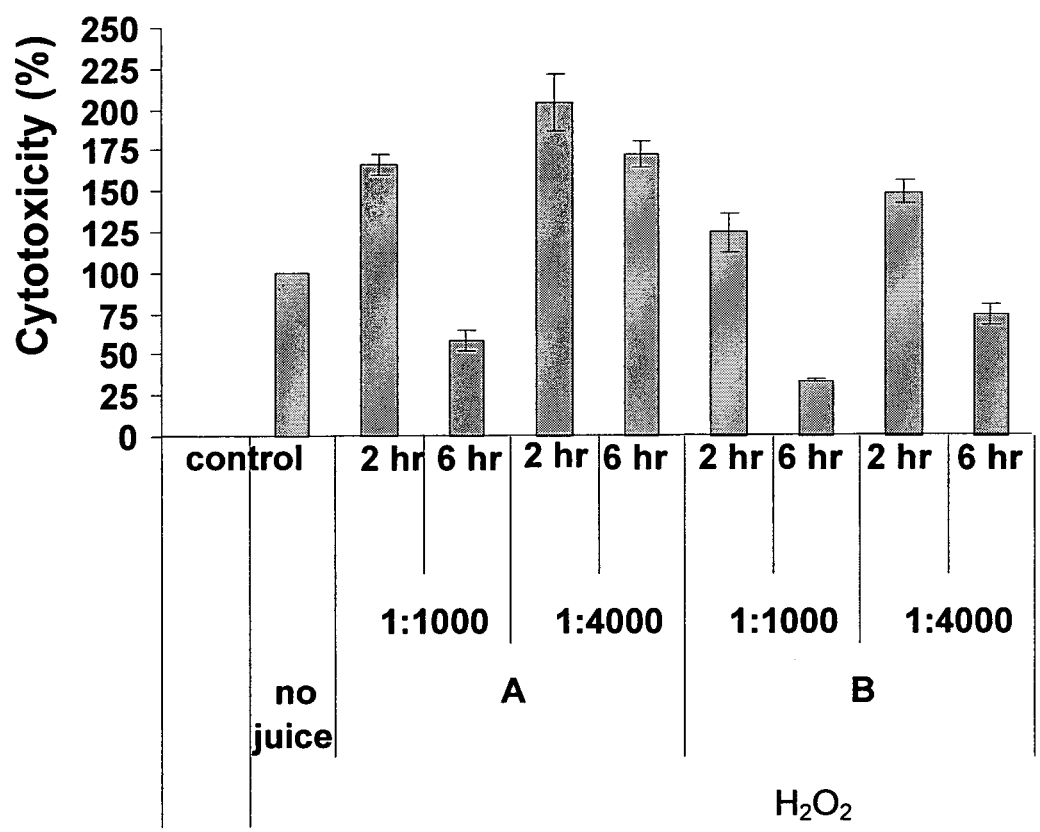
FIG. 13 shows the percentage of measured cytotoxicity for astrocytes preincubated with two concentrations of marula juice (A) and extract I (B) for 2 hr or 6 hrs before the oxidative insult. The results are the mean±SD of an experiment performed in tetraplicates.

In another experiment, the effect of the incubation time and of the concentration was tested with 2 dilutions (1:1000 or 1:4000) of each juice, filtered marula juice and extract I, for 2 or 6 hr before the addition of $H_2O_2$ (FIG. 13). Extract I was found most efficient (70% protection). Filtered marula juice also exhibited a significant protective activity (40% protection).

4. Clinical Protocol

Ten healthy volunteers (Table 1), non-smokers, and with no metabolic disorders, with plasma cholesterol levels lower than 200 mg/dl and under no drug treatment, were recruited for the study. All subjects signed a consent form before entering the study. The study protocol was approved by the Rambam Helsinki Committee (No. 2452).

TABLE 1

Classification of study volunteers.

| Name | Age | Gender | Medications | Smoking |
|------|-----|--------|-------------|---------|
| SG | 21 | M | None | No |
| SY | 21 | M | None | No |
| VP | 43 | M | None | No |
| KA | 21 | M | None | No |
| EY | 22 | M | None | No |
| BTK | 27 | M | None | No |
| DE | 57 | M | None | No |
| RR | 24 | M | None | No |
| FY | 40 | M | None | No |
| GG | 37 | M | None | No |

All participants consumed 200 mL of pasteurized juice per day, with their main meal, for a period of 3 weeks. All subjects included in the study continued with their habitual life style. Blood pressure was measured at time zero (before study entry), after 3 weeks, and at the end of the study (after 4 weeks of washout). Blood samples (25 mL) were collected for analyses at time zero (Baseline—before study entry), after 3 weeks of marula juice consumption, and 4 weeks after the end of juice consumption (washout).

All blood serum samples were frozen at −80° C. until analyses. Biochemical analyses in serum were performed by employing commercially available diagnostic kits, and included measurement of glucose, calcium, kidney function (BUN, creatinine and the electrolytes natrium and kalium), liver function (CK, AST and total bilirubin), total cholesterol, HDL—cholesterol, LDL-cholesterol and total triglycerides. Uric acid levels (as a possible antioxidant) in serum were measured using a commercially available kit.

Oxidative Stress Analyses of Serum Samples

Ferric-Reducing Antioxidant Power (FRAP): Working FRAP reagent was prepared by mixing 25 ml acetate buffer, 2.5 ml 2,4,6-Tripyridyl-s-Triazine (TPTZ) solution, and 2.5 ml $FeCL_3*6H_2O$ solution. Aqueous solutions of 1 mM $FeSO_4*7H_2O$ at concentrations of 5, 10, 20, 30, 40, 50 and 100 mM were used for a standard calibration curve. FRAP reagent (freshly prepared) was warmed to 37° C. and a reagent blank was read at 593 nm spectrophotometrically. Serum sample (30 µl) was mixed with 90 µl of water. Then, 900 µl of the FRAP reagent were added and mixed quickly. Absorbance was read after 0.5 second and every 15 seconds during 4 minutes. The change in absorbance ($A_{593\ nm}$) between the final and the initial optical density was calculated for each sample and was then related to $Fe^{+2}$ concentration in the standard curve (tested in parallel).

Serum Lipid Peroxidation

Serum was diluted 1:4 (v:v) with phosphate buffered saline (PBS) and then incubated in the absence or presence of 100 mmol/L of the free radical generator 2,2'-azobis-2-amidinopropane hydrochloride (AAPH) for 2 hours at 37° C. Serum lipid peroxidation was determined by measuring the generated amount of thiobarbituric acid reactive substances (TBARS) and of lipid peroxides using spectrophotometric methods. The lipid peroxide (PD) test analyzes lipid peroxide formation by their capacity to convert iodide to iodine after incubation for 18 hours at 25° C., as measured spectrophotometrically at 365 nm.

As results of the study indicate, consumption had no significant effect on blood pressure; serum levels of glucose and calcium were not significantly altered after consumption and kidney function tests were not significantly affected by the continued consumption. Similarly, the consumption resulted in substantially unaltered electrolyte blood level and liver function. However, serum triglyceride levels decreased by 7% after consumption, with the effect persisting after the 4-week washout period (Table 2).

TABLE 2

Effect of juice consumption on serum triglyceride concentrations.

| | Triglycerides | | |
|---|---|---|---|
| Subjects | 0 | 3 weeks | Washout |
| 1 | 79 | 79 | 71 |
| 2 | 74 | 93 | 92 |
| 3 | 153 | 163 | 140 |
| 4 | 48 | 40 | 47 |
| 5 | 66 | 71 | 82 |
| 6 | 188 | 121 | 119 |
| 7 | 147 | 147 | 158 |
| 8 | 56 | 61 | 87 |
| 9 | 109 | 85 | 101 |
| 10 | 196 | 180 | 77 |
| Average | 112 | 104 | 97 |
| SD | 55 | 47 | 33 |

Consumption over a period of 3 weeks, significantly ($p<0.02$) reduced the concentrations of total cholesterol in serum by 8% (Table 3).

TABLE 3

Effect of consumption on serum cholesterol concentrations

| | Total Cholesterol | | | LDL-Cholesterol | | | HDL-Cholesterol | | |
|---|---|---|---|---|---|---|---|---|---|
| Subjects | 0 | 3 wks | Washout | 0 | 3 wks | Washout | 0 | 3 wks | Washout |
| 1 | 250 | 245 | 235 | 144 | 119.7 | 115.91 | 90.6 | 109.5 | 104.89 |
| 2 | 152 | 141 | 153 | 93 | 67.2 | 81.95 | 44.2 | 55.2 | 52.65 |
| 3 | 237 | 182 | 243 | 166 | 112.8 | 171.71 | 40.1 | 36.6 | 43.29 |
| 4 | 151 | 143 | 166 | 86 | 59.6 | 86.12 | 54.9 | 75.4 | 70.48 |
| 5 | 169 | 148 | 139 | 95 | 72.4 | 73.22 | 61.2 | 61.4 | 58.95 |
| 6 | 152 | 142 | 147 | 72 | 69.3 | 73.82 | 42 | 48.5 | 49.38 |
| 7 | 177 | 142 | 179 | 104 | 64.1 | 108.03 | 43.2 | 39.3 | 39.37 |
| 8 | 171 | 181 | 210 | 104 | 104.9 | 129.82 | 56 | 63.9 | 62.78 |
| 9 | 256 | 221 | 221 | 175 | 153.6 | 149.09 | 59.5 | | 51.71 |
| 10 | 194 | 209 | 215 | 113 | 131.1 | 160.7 | 41.7 | 41.9 | 38.9 |
| Average | 191 | 175.4 | 190.8 | 115 | 95.47 | 115.037 | 53.3 | 59.08 | 57.24 |
| SD | 41.6 | 38.5 | 38.4846 | 34.7 | 33.19 | 36.6718 | 15.4 | 22.79 | 19.5595 |
| p value | | 0.02 | | | 0.01 | | | 0.03 | |

This reduction may be related to a significant ($p<0.01$) reduction in LDL-cholesterol levels, by 17%. However, these reductions did not persist after the washout period, as the levels of total cholesterol, as well as those of LDL-cholesterol, returned to baseline levels after 4 weeks of washout period, during which the subject did not consume the juice. The serum level of HDL-cholesterol increased significantly ($p<0.03$) by 10% after consumption of the juice and this reduction persisted, though at a lower extent (by only 7%), after the washout period.

Table 4 shows the effect on serum oxidative stress. Serum samples were subjected to AAPH-induced oxidation. Lipid peroxide formation was significantly ($p<0.03$) decreased in serum samples derived after consumption for 3 weeks. However, this effect was not sustained after the washout period. In serum samples derived after consumption, the "antioxidant power", measured by the FRAP assay, increased during the consumption period, and even further increased, reaching a significant elevation of 8% after the washout period. The reduction in serum oxidative stress may be the result of the reduction in serum lipid concentrations (less substrate available for oxidation, as well as the effect of marula juice potent antioxidants).

TABLE 4

Effect on Serum Oxidative Stress

| | PD | | | FRAP | | |
|---|---|---|---|---|---|---|
| Subjects | 0 | 3 weeks | Washout | 0 | 3 weeks | Washout |
| 1 | 798 | 776 | 797 | 837 | 912 | 751 |
| 2 | 738 | 728 | 733 | 781 | 864 | 897 |
| 3 | 735 | 715 | 839 | 733 | 661 | 691 |
| 4 | 798 | 772 | 847 | 615 | 651 | 719 |
| 5 | 730 | 701 | 758 | 605 | 734 | 613 |
| 6 | 577 | 567 | 620 | 1091 | 1041 | 1048 |
| 7 | 615 | 626 | 634 | 767 | 814 | 933 |
| 8 | 681 | 660 | 659 | 802 | 850 | 948 |
| 9 | 683 | 711 | 668 | 653 | 663 | 767 |
| 10 | 696 | 636 | 615 | 917 | 842 | 1069 |
| Average | 705.10 | 689.20 | 717.00 | 780.10 | 803.20 | 843.60 |
| SD | 71.13 | 66.49 | 89.81 | 147.42 | 126.37 | 156.62 |
| p value | | 0.03 | | | | 0.03 |

Figure 14A:
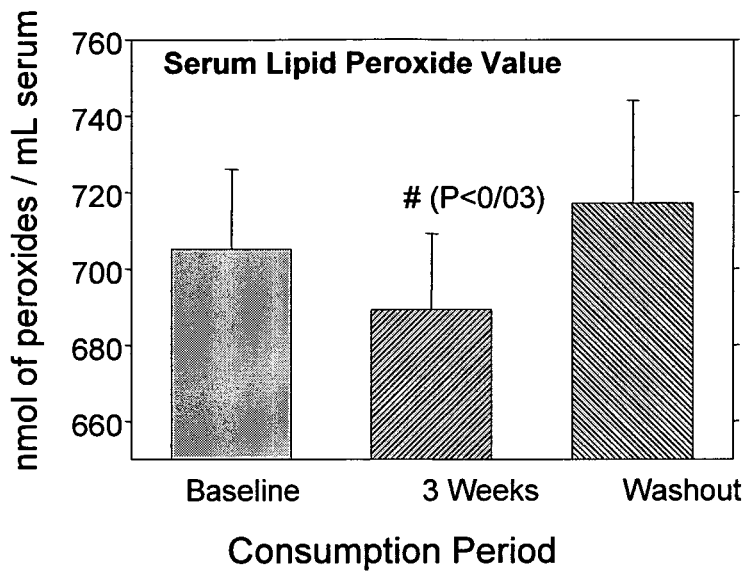
FIGS. 14A-B shows the antioxidative effects of marula juice in vitro (FIG. 14A—Lipid peroxide formation.
Figure 14B:
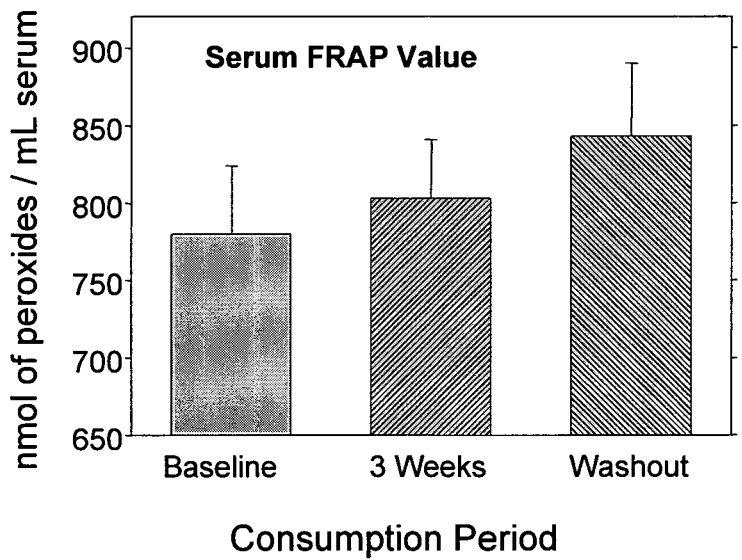

The effect of pasteurized juice consumption on serum oxidative stress is summarized in FIGS. 14A-B. Serum samples were subjected to AAPH-induced oxidation. Lipid peroxide formation (FIG. 14A) was significantly ($p<0.03$) decreased in serum samples derived after consumption of the juice over a period of 3 weeks. This effect was not sustained after the washout period. The antioxidant power capacity, measured by the FRAP assay (FIG. 14B), increased in serum samples derived after consumption of pasteurized marula juice, and surprisingly, even further increased, reaching a significant elevation of 8%, after the washout period.

The invention claimed is:

1. A method for the treatment of atherosclerosis in a mammal, comprising:
    administering a therapeutically effective amount of an extract, or a pharmaceutical composition comprising the extract, to the mammal, the extract being prepared by a process comprising
        drying marula juice into a solid or semi solid mass,
        contacting the solid or semi solid mass with an organic solvent to obtain a suspension, and
        optionally centrifuging the suspension to separate a liquid phase that comprises the extract from a solid phase.
2. The method according to claim 1, wherein the organic solvent is ethanol or an aqueous solution comprising ethanol.
3. The method according to claim 2, wherein the ethanol is present in the aqueous solution in an amount of at least 50%.

* * * * *